US012682642B2

(12) United States Patent
Wang et al.

(10) Patent No.: US 12,682,642 B2
(45) Date of Patent: Jul. 14, 2026

(54) SYSTEM AND METHOD FOR PATIENT MANAGEMENT USING MULTI-DIMENSIONAL ANALYSIS AND COMPUTER VISION

(71) Applicant: ALL INSPIRE HEALTH, INC., Dover, DE (US)

(72) Inventors: Michael Y. Wang, New York, NY (US); Vincent James Cocito, Maplewood, NJ (US); Paul Ensom Coyne, Hoboken, NJ (US); Jeffrey Morelli, Westfield, NJ (US)

(73) Assignee: All Inspire Health, Inc., Dover, DE (US)

( * ) Notice: Subject to any disclaimer, the term of this patent is extended or adjusted under 35 U.S.C. 154(b) by 21 days.

(21) Appl. No.: 17/512,184

(22) Filed: Oct. 27, 2021

(65) Prior Publication Data

US 2022/0122722 A1 Apr. 21, 2022

Related U.S. Application Data

(63) Continuation of application No. 15/618,357, filed on Jun. 9, 2017, now abandoned.

(51) Int. Cl.
*G06V 20/52* (2022.01)
*G01S 1/68* (2006.01)
(Continued)

(52) U.S. Cl.
CPC ................ *G06V 20/52* (2022.01); *G01S 1/68* (2013.01); *G06F 18/214* (2023.01); *G06F 18/24* (2023.01);
(Continued)

(58) Field of Classification Search
CPC ........ G16H 40/20; H04N 5/232; H04N 7/183; G06T 7/70; G06T 2207/30196;
(Continued)

(56) References Cited

U.S. PATENT DOCUMENTS 9,300,925 B1 3/2016 Zhang
9,728,209 B2 8/2017 Chen et al.
(Continued)

FOREIGN PATENT DOCUMENTS

EP 4006589 A1 * 6/2022 ............. G01S 19/48
WO WO-2016099084 A1 * 6/2016

OTHER PUBLICATIONS

"U.S. Appl. No. 15/618,357, Examiner Interview Summary mailed Jan. 13, 2021", 2 pgs.
(Continued)

*Primary Examiner* — Alaaeldin M. Elshaer
(74) *Attorney, Agent, or Firm* — Schwegman Lundberg & Woessner, P.A.

(57) ABSTRACT

The disclosed embodiments include a system and method for patient management using multi-dimensional analysis and computer vision. The system includes a base unit having a microprocessor connected to a camera and a beacon detector. The beacon detector scans for advertising beacons with a packet and publishes a packet to the microprocessor. The camera captures an image in a pixel array and publishes image data to the microprocessor. The microprocessor uses at least a Beacon ID from the packet to determine if an object is in a room, and Camera Object Coordinates from the image data to determine the coordinates of the object in the room.

26 Claims, 26 Drawing Sheets

(51) Int. Cl.

| | |
|---|---|
| *G06F 18/214* | (2023.01) |
| *G06F 18/24* | (2023.01) |
| *G06T 7/70* | (2017.01) |
| *G16H 40/20* | (2018.01) |
| *H04N 7/18* | (2006.01) |

(52) U.S. Cl.
CPC ............... *G06T 7/70* (2017.01); *G16H 40/20* (2018.01); *H04N 7/183* (2013.01); *G06T 2207/30196* (2013.01)

(58) Field of Classification Search
CPC ...... G06V 20/52; G06V 10/10; G06V 10/751; G06K 9/00; G06K 9/6256; G06K 9/6267; G06K 7/10; G01S 1/68; H04W 4/02
USPC ........................................................ 705/2, 3
See application file for complete search history.

(56) References Cited

U.S. PATENT DOCUMENTS

| | | | |
|---|---|---|---|
| 2012/0154582 | A1 | 6/2012 | Johnson et al. |
| 2012/0249802 | A1 | 10/2012 | Taylor |
| 2012/0262365 | A1* | 10/2012 | Mallinson ............... G06F 3/017 |
| | | | 345/156 |
| 2013/0085609 | A1 | 4/2013 | Barker |
| 2013/0103419 | A1 | 4/2013 | Beaudry |
| 2015/0109442 | A1* | 4/2015 | Derenne ................ H04N 7/185 |
| | | | 348/143 |
| 2016/0242681 | A1* | 8/2016 | Shen ...................... A61B 5/742 |
| 2017/0109481 | A1 | 4/2017 | Johnson et al. |
| 2017/0124366 | A1* | 5/2017 | Good ...................... H04W 4/80 |
| 2017/0142323 | A1* | 5/2017 | Saito ......................... G06T 7/70 |
| 2017/0187991 | A1 | 6/2017 | Törös et al. |
| 2017/0193177 | A1* | 7/2017 | Kusens ............... G08B 13/196 |
| 2018/0055384 | A1 | 3/2018 | Ambili et al. |
| 2018/0357380 | A1 | 12/2018 | Wang et al. |
| 2019/0098206 | A1* | 3/2019 | Hong ................. G06F 16/5866 |
| 2019/0327161 | A1 | 10/2019 | Cannell et al. |

OTHER PUBLICATIONS

"U.S. Appl. No. 15/618,357, Final Office Action mailed Mar. 27, 2020", 14 pgs.

"U.S. Appl. No. 15/618,357, Final Office Action mailed Apr. 27, 2021", 31 pgs.

"U.S. Appl. No. 15/618,357, Non Final Office Action mailed Oct. 22, 2020", 15 pgs.

"U.S. Appl. No. 15/618,357, Non Final Office Action mailed Dec. 20, 2019", 13 pgs.

"U.S. Appl. No. 15/618,357, Response filed Jan. 20, 2021 to Non Final Office Action mailed Oct. 22, 2020", 10 pgs.

"U.S. Appl. No. 15/618,357, Response filed Mar. 20, 2020 to Non Final Office Action mailed Dec. 20, 2019", 7 pgs.

"U.S. Appl. No. 15/618,357, Response filed Sep. 10, 2020 to Final Office Action mailed Mar. 27, 2020", 7 pgs.

"U.S. Appl. No. 15/618,357, Response filed Nov. 25, 2019 to Restriction Requirement mailed Jun. 25, 2019", 6 pgs.

"U.S. Appl. No. 15/618,357, Restriction Requirement mailed Jun. 25, 2019", 6 pgs.

"International Application Serial No. PCT/US2018/036574, International Search Report mailed Aug. 27, 2018", 3 pgs.

* cited by examiner

EAR

SHOULDER

ELBOWS

HIPS

KNEE

ANKLE

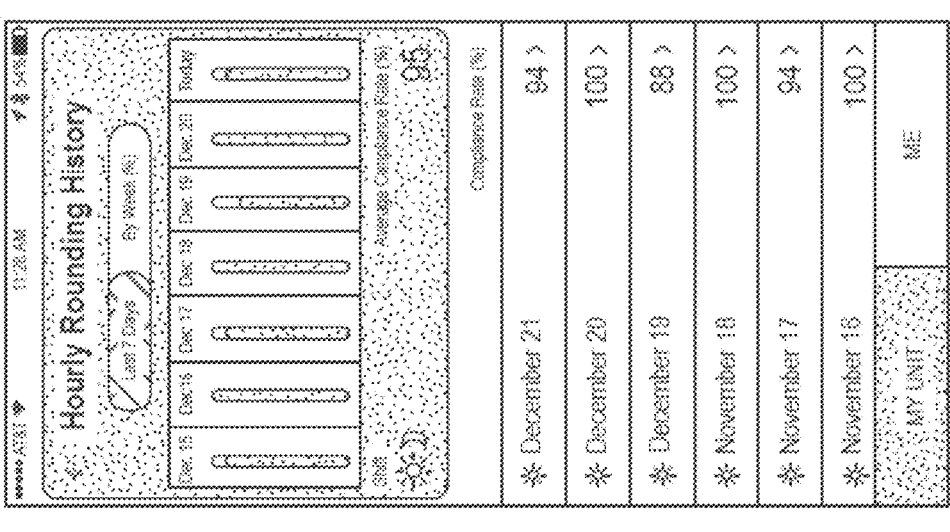
FIG. 13C
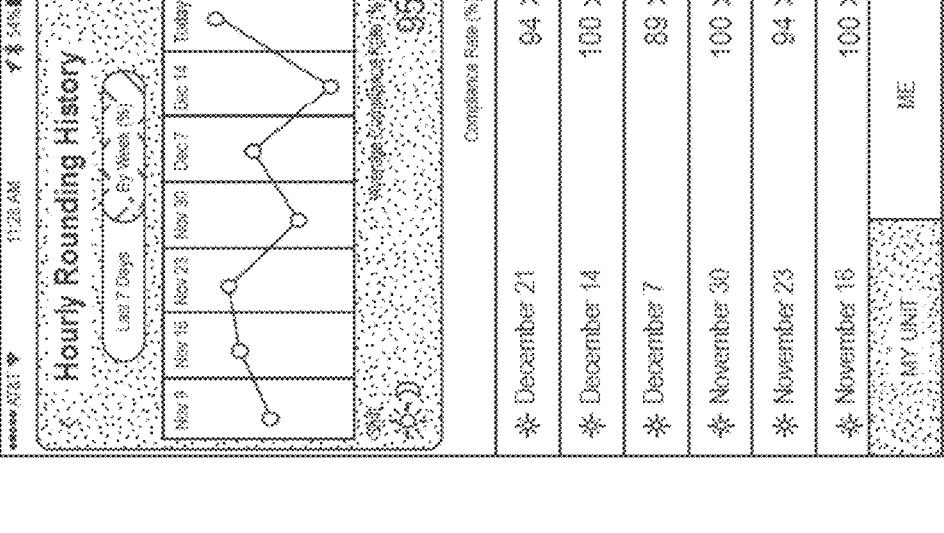
FIG. 13B
FIG. 13A

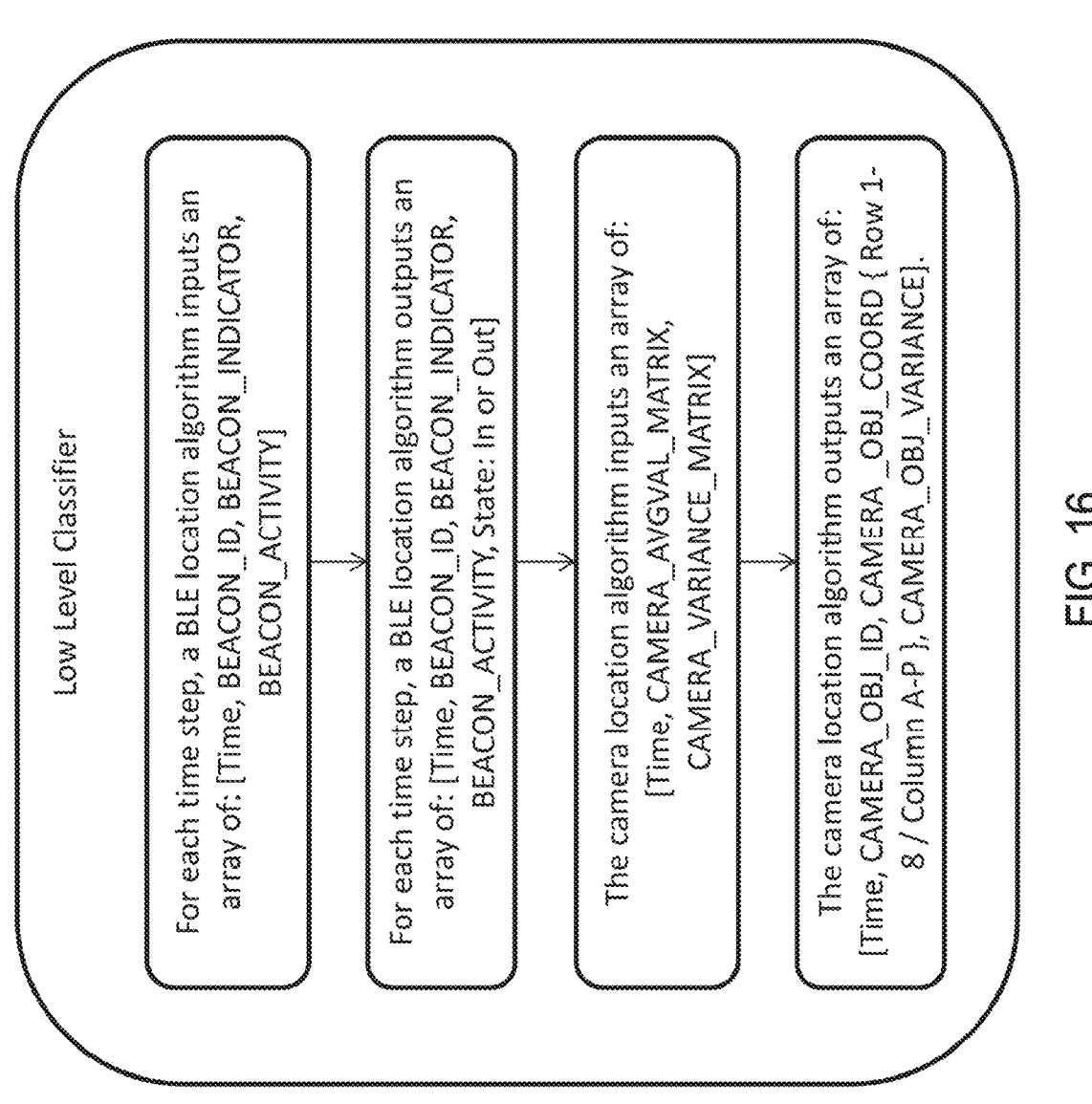

Low Level Classifier

For each time step, a BLE location algorithm inputs an array of: [Time, BEACON_ID, BEACON_INDICATOR, BEACON_ACTIVITY]

For each time step, a BLE location algorithm outputs an array of: [Time, BEACON_ID, BEACON_INDICATOR, BEACON_ACTIVITY, State: In or Out]

The camera location algorithm inputs an array of: [Time, CAMERA_AVGVAL_MATRIX, CAMERA_VARIANCE_MATRIX]

The camera location algorithm outputs an array of: [Time, CAMERA_OBJ_ID, CAMERA_OBJ_COORD { Row 1-8 / Column A-P }, CAMERA_OBJ_VARIANCE].

FIG. 16

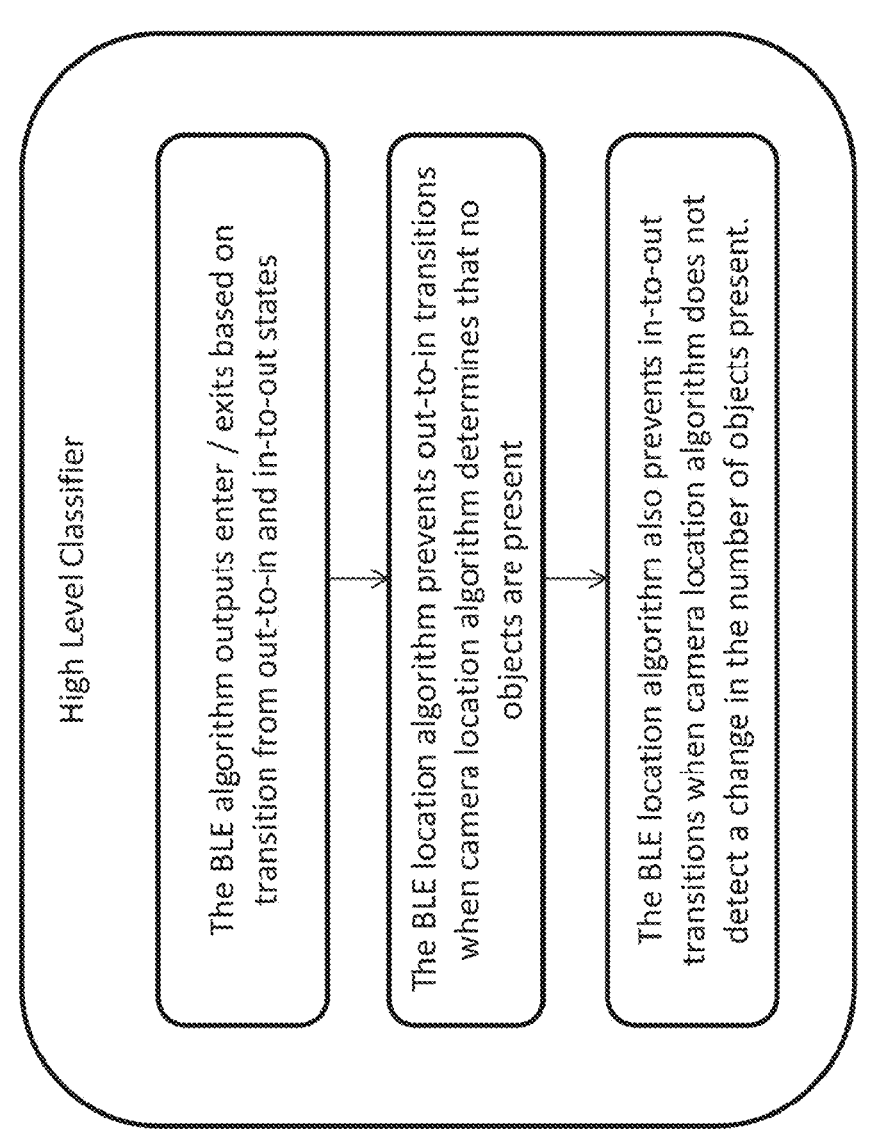

High Level Classifier

The BLE algorithm outputs enter / exits based on transition from out-to-in and in-to-out states The BLE location algorithm prevents out-to-in transitions when camera location algorithm determines that no objects are present The BLE location algorithm also prevents in-to-out transitions when camera location algorithm does not detect a change in the number of objects present.

FIG. 17A

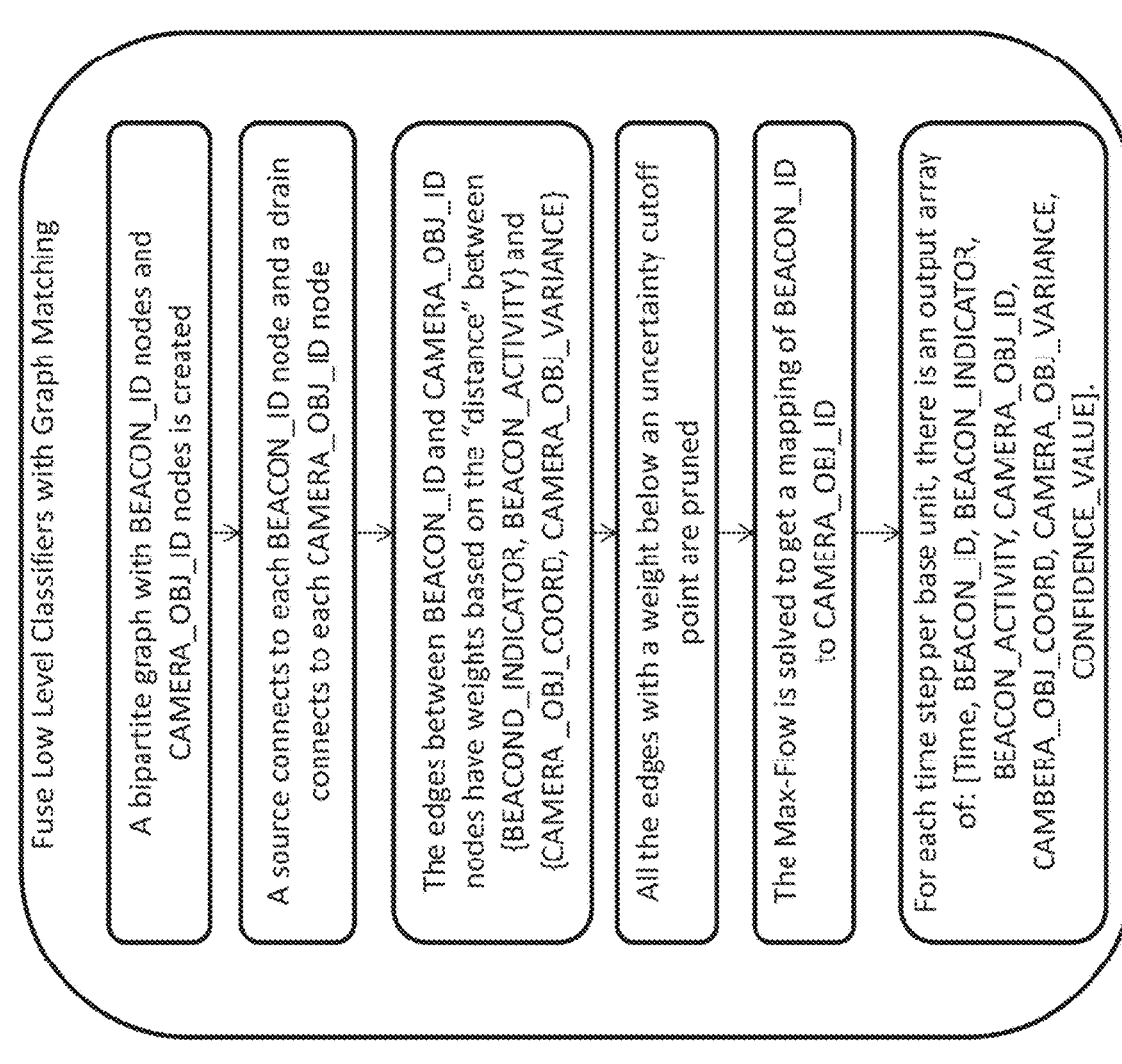

Fuse Low Level Classifiers with Graph Matching

A bipartite graph with BEACON_ID nodes and CAMERA_OBJ_ID nodes is created

A source connects to each BEACON_ID node and a drain connects to each CAMERA_OBJ_ID node The edges between BEACON_ID and CAMERA_OBJ_ID nodes have weights based on the "distance" between {BEACOND_INDICATOR, BEACON_ACTIVITY} and {CAMERA_OBJ_COORD, CAMERA_OBJ_VARIANCE}

All the edges with a weight below an uncertainty cutoff point are pruned

The Max-Flow is solved to get a mapping of BEACON_ID to CAMERA_OBJ_ID

For each time step per base unit, there is an output array of: [Time, BEACON_ID, BEACON_INDICATOR, BEACON_ACTIVITY, CAMERA_OBJ_ID, CAMERA_OBJ_COORD, CAMERA_OBJ_VARIANCE, CONFIDENCE_VALUE].

FIG. 17B

SYSTEM AND METHOD FOR PATIENT MANAGEMENT USING MULTI-DIMENSIONAL ANALYSIS AND COMPUTER VISION

This application is a continuation of U.S. patent application Ser. No. 15/618,357, filed Jun. 9, 2017, which is incorporated by reference herein in its entirety.

BACKGROUND

1. Field of Invention

The present invention relates generally to a human presence detection, identification, recording and differentiation apparatus, and more particularly to a wireless, wall-mounted device that can detect, identify, locate, record, interpret, and differentiate human presence using a camera and beacon detector.

2. Background of Art

It is common today that elderly individuals or individuals with chronic illness or disabilities obtain specialized care as a patient in a long-term healthcare facility. Often, the family members of the patients feel disconnected from the day-to-day care that the patient receives. As such, many family members of patients express concern that the vulnerable patient may be neglected or abused. Even in a more privatized healthcare setting, such as a where a patient has a personal at-home nurse, harm to the patient is still a concern to family members.

Traditionally, hospitals and other healthcare facilities have attempted to resolve patient neglect problems through the installation of cameras for video monitoring around hospital rooms and care facilities. However, video monitoring and other human-monitored imaging systems in the patient room are not realistic solutions to the problem as they encroach on the privacy of the patient and require vigilant and time-consuming review by family members. Outside the patient care setting, imaging systems have been utilized to track people due to their simple lens, which can be used to precisely aim receivers at an area of interest. In addition, imaging systems are insensitive to body positioning if they are not specifically programmed for facial identification and can thus track individuals despite numerous small body movements. Also, imaging systems are useful to track people because visible or near-visible light does not bleed through walls. However, imaging systems have many limitations. For example, reliably identifying an individual from an image is a difficult problem. In another example, imaging systems pose potential privacy problems, as similarly stated above, especially if the system captures identifiable information about people who have not consented to being tracked.

Alternative monitoring systems have used real-time locating systems (RTLS) where objects and consenting individuals are given tracking devices, such as Bluetooth Low Energy (BLE) beacons, infrared transmitters, and passive RFID. RTLS systems have a distinct advantage over camera based systems at identifying tracked objects as the ID of the person or object is digitally encoded in the data transmitted by the device.

However, achieving precise locating information from RTLS systems traditionally involves substantial tradeoffs. RTLS systems often require multiple pieces of installed infrastructure that require ceiling mounting and cabling to enable the triangulation or trilateration required to achieve meter- or sub-meter level accuracy. Furthermore, the potential for measuring more detail such as a person's skeletal orientation from RTLS is not possible without adding devices to the person. In addition, the tracked devices themselves often employ proprietary technology that imposes high cost and locks in users.

Therefore, there is a need for a system that can accurately and precisely identify and locate objects and consenting people without compromising the privacy of non-consenting individuals and without locking in hospitals to expensive, proprietary infrastructure.

SUMMARY OF THE INVENTION

In accordance with the foregoing objects and advantages, various aspects and embodiments of the present invention provide a system and method for patient management using multi-dimensional analysis and computer vision.

In one embodiment, the system includes a base unit having a microprocessor connected to a camera and a beacon detector. The beacon detector scans for advertising beacons with a packet and publishes the packet to the microprocessor. The camera captures an image in a pixel array and publishes image data to the microprocessor. The microprocessor uses at least a Beacon ID from the packet to determine if an object is in a room, and Camera Object Coordinates from the image data to determine the coordinates of the object in the room.

In another embodiment, the method for detecting body position in a confined space includes the steps of providing a base unit having a microprocessor connected to a beacon detector and a camera. The beacon detector receives an advertisement from a beacon with a packet having at least a Beacon ID. The microprocessor determines if an object is in the confined space based at least in part on the Beacon ID. The camera captures a pixel array of the confined space, which is processed into imaging data. The microprocessor receives the imaging data and determines the coordinates of the object in the confined space using Camera Object Coordinates from the imaging data.

In another embodiment, the method above further includes the steps of providing a second base unit having a microprocessor connected to a beacon detector and a camera to detect body position in a second confined space. The second base unit receives an advertisement from a beacon with a packet at the beacon detector and determines, via the microprocessor, if the object is in the second confined space based at least in part on the Beacon ID from the packet. The camera captures a pixel array of the second confined space, which is processed into imaging data. The microprocessor receives the imaging data and determines the coordinates of the object in the second confined space using Camera Object Coordinates from the imaging data. Finally, the system determines a current state for each Beacon ID of the BLE beacon across the first base unit and the second base unit.

In an alternative embodiment, the method for automating the measurement and feedback of patient care, includes the step of first, providing a system having a base unit with a microprocessor connected to: (i) a camera, which transmits coordinate information to the microprocessor, (ii) a sensor, and (iii) a beacon detector, which scans for advertising beacons and publishes a packet to the microprocessor. Next, the method includes the steps of correlating data from the sensor, presence information, and coordinate information to determine a patient care event, and publishing the patient care event to a web application interface. Such patient care event publications can be used to assign the patient care event to a healthcare provider and determine a rate of compliance based on the number of patient care events per unit of time.

In another embodiment, the method for inferring patient care activity from sensor data, includes the steps of first, providing a system with a base unit having a microprocessor connected to: (i) a camera, which transmits coordinate information to the microprocessor, (ii) a sensor, and (iii) a beacon detector, which scans for advertising beacons and publishes a packet to the microprocessor, and a label database, which stores electronic record data. Next, the method includes the steps of creating a scene model for the electronic record data via a scene classifier trainer, receiving a feature comprised of presence information, data from the sensor, and coordinate information, and classifying the feature through comparison of the feature to the scene model.

BRIEF DESCRIPTION OF THE DRAWINGS

Embodiments and aspects of the present invention will be more fully understood and appreciated by reading the following Detailed Description in conjunction with the accompanying drawings, in which:

FIG. 13A is a perspective view of an illustrative embodiment of a Hourly Rounding analysis interface;

FIG. 13B is a perspective view of an illustrative embodiment of a Hourly Rounding History interface;

FIG. 13C is a perspective view of an illustrative embodiment of an alternative Hourly Rounding History interface;

FIG. 16 is a flowchart of an illustrative embodiment of a method for low level classification;

FIG. 17A is a flowchart of an illustrative embodiment of a method for high level classification;

FIG. 17B is a flowchart of an alternative illustrative embodiment of a method for high level classification;

DETAILED DESCRIPTION

Referring to the Figures, the present invention may be a system, a method, and/or a computer program product. The computer program product may include a computer readable storage medium (or media) having computer readable program instructions thereon for causing a processor to carry out aspects of the present invention.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

An embodiment of the invention is a system comprising a wireless, wall-mounted base unit that can detect, identify, locate, record, and differentiate activities involving humans and objects equipped with machine identifiable devices such as beacons. The present invention also offers a mobile application platform that allows health facility unit managers analyze real-time data on safety protocols, analyze patient demand, create and view staff assignments (past and present), and enables family members to know when a loved one is receiving professional care.

Figure 1:
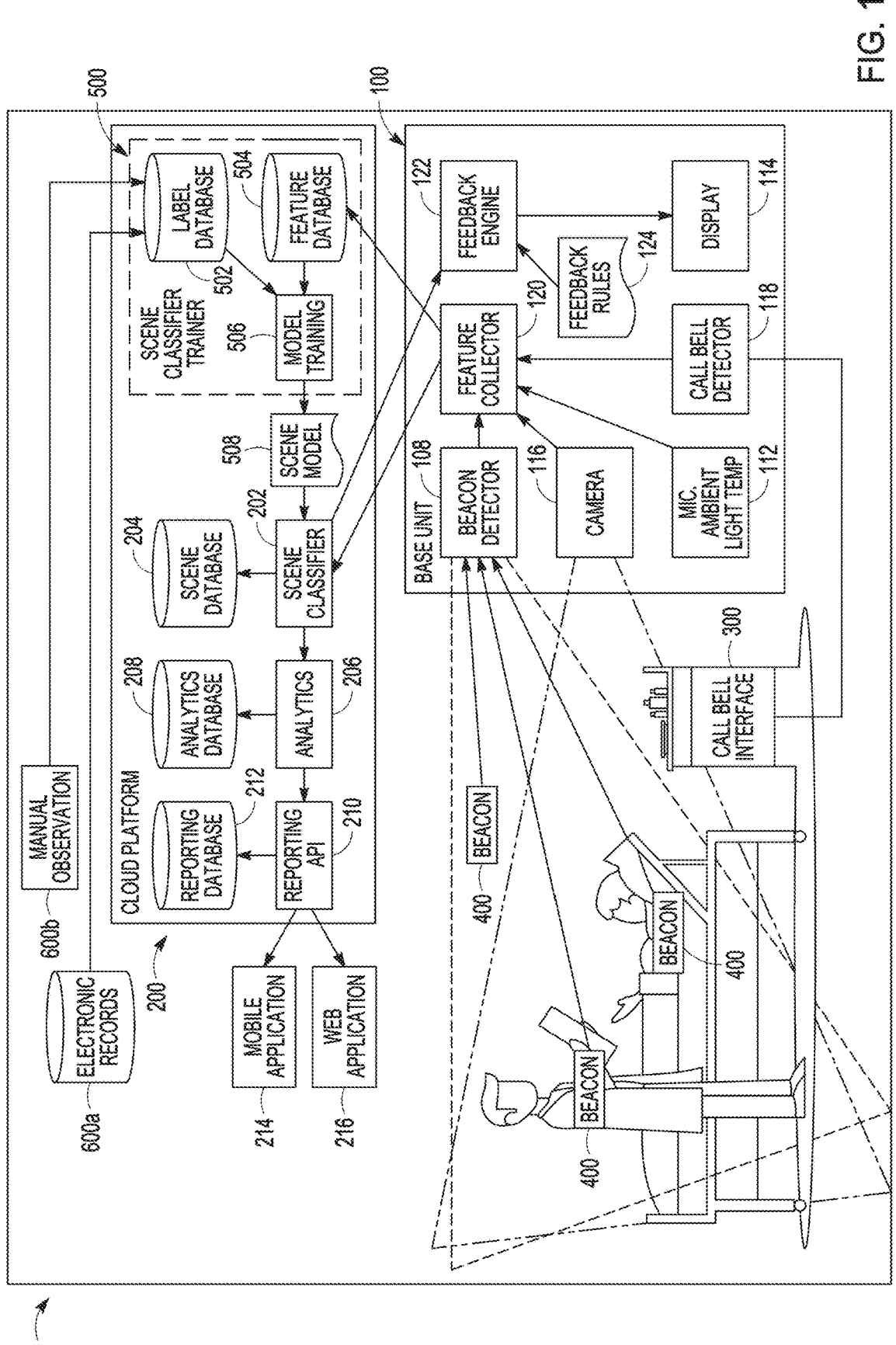
FIG. 1 is a diagram of an illustrative embodiment of the positioning system.
Figure 2:
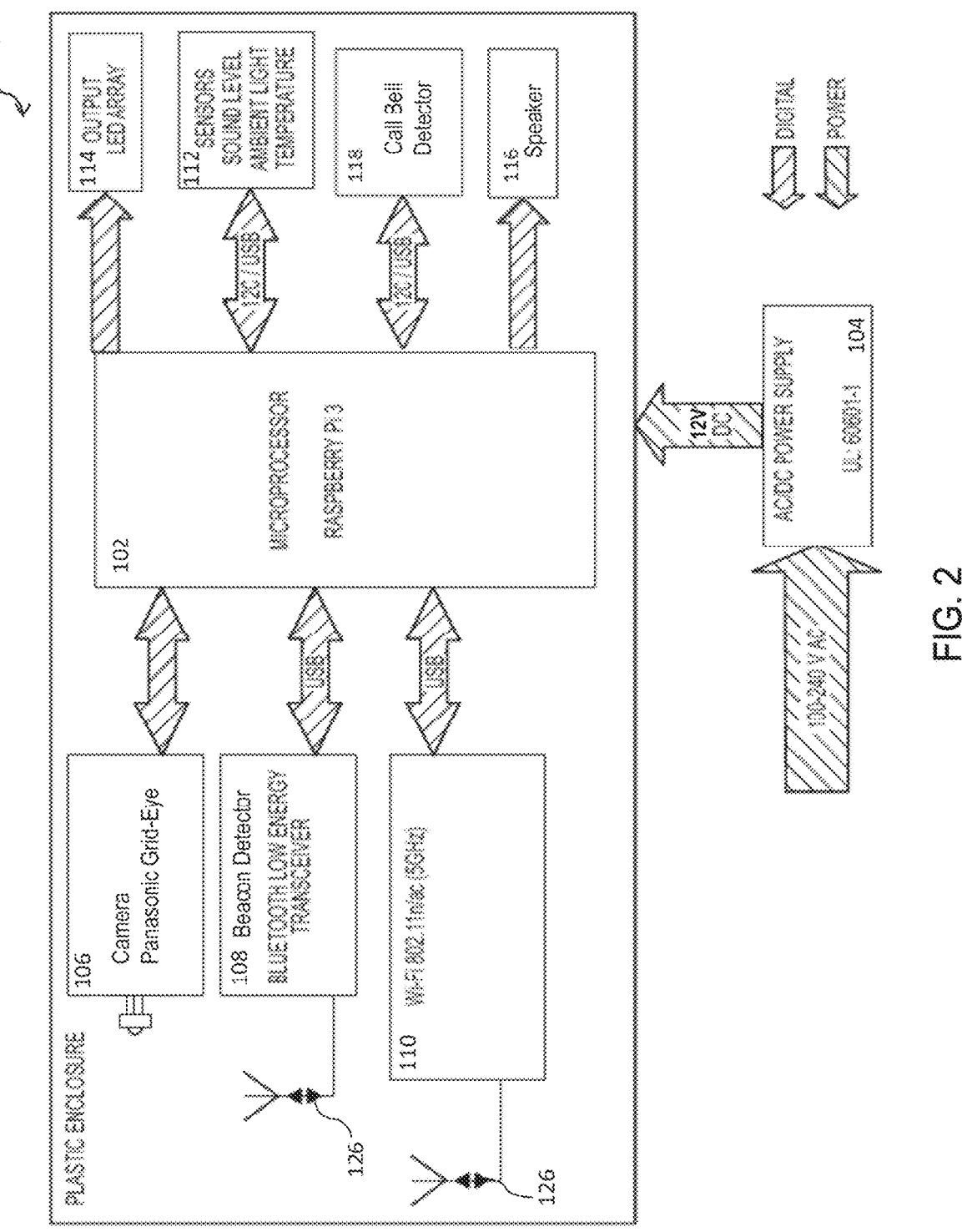
FIG. 2 is a diagram of an illustrative embodiment of the components of the base unit.

Referring first to FIG. 1, there is shown a diagram of an illustrative embodiment of the positioning system 10. The positioning system 10 comprises a base unit 100 wirelessly connected to a cloud platform 200. FIG. 2 shows a diagram of an illustrative embodiment of the components of the base unit 100. The embodiment shown in FIG. 2 utilizes a Computer Vision—Beacon Sensor Fusion hybrid positioning system 10. The base unit 100 comprises a microprocessor 102, such as a Raspberry Pi 3, powered by an AC/DC power supply 104. The microprocessor 102 shown in FIG. 2, may comprise the feature collector 120, feedback engine 122, and feedback rules 124 shown in FIG. 1. The microprocessor 102 both transmits digital data to and receives digital data from a camera 106 (e.g., Panasonic Grid-Eye), a beacon detector (Ubertooth Bluetooth Low Energy transceiver) 108, a Wi-Fi transceiver 110, a display 114, a call bell detector 118, and one or more sensors 112. Such sensors 112 may detect sound level, ambient light, and temperature, for example.

As described later, the microprocessor 102 uses data received from the camera 106, beacon detector 108, and sensors 112 to identify individuals in a room and determine their body positioning. These listed features are connected to the microprocessor 102 via USB or I2C. In addition, the base unit 100 comprises a spiral antenna 126 with a ground plane connected to the beacon detector 108 to focus reception on the bed area in front of the base unit. The base unit 100 also includes a Wi-Fi module 110 and antenna 126. However, alternative antennae 126 can be substituted for the transmission and reception of digital data for both the beacon detector 108 and Wi-Fi module 110.

Referring back to FIG. 1, the base unit 100 is also shown comprising a call bell detector 118, a feature collector 120, and a feedback engine 122, which are also connected to the microprocessor 102 such as to exchange digital data with the microprocessor 102. The call bell detector 118 receives data from a call bell interface 300 in the hospital or healthcare facility room. The base unit 100 receives data at the call bell detector 118 when a patient, healthcare provider, or other individual in the room activates a call bell at the call bell interface 300. The call bell interface 300 can be the existing call bell system in a healthcare facility and the call bell detector 118 will passively connect thereto.

Figure 21A:
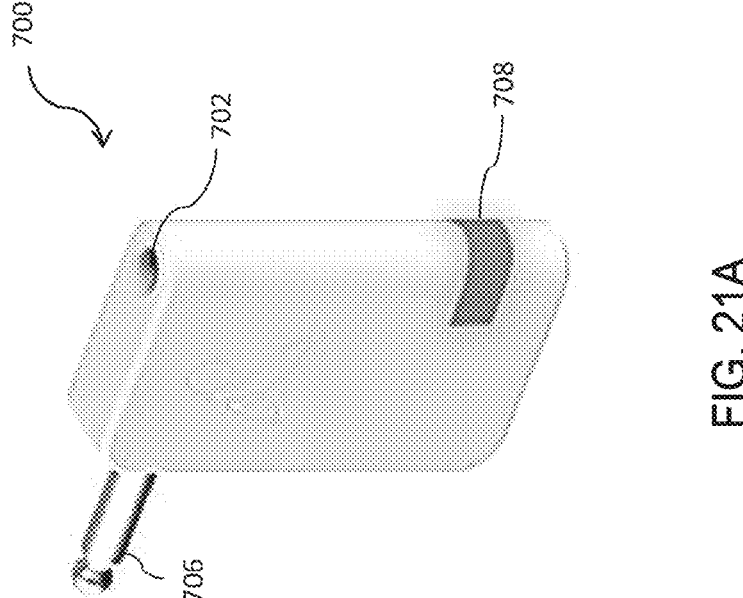
FIG. 21A is a perspective view of a call bell accessory.
Figure 21B:
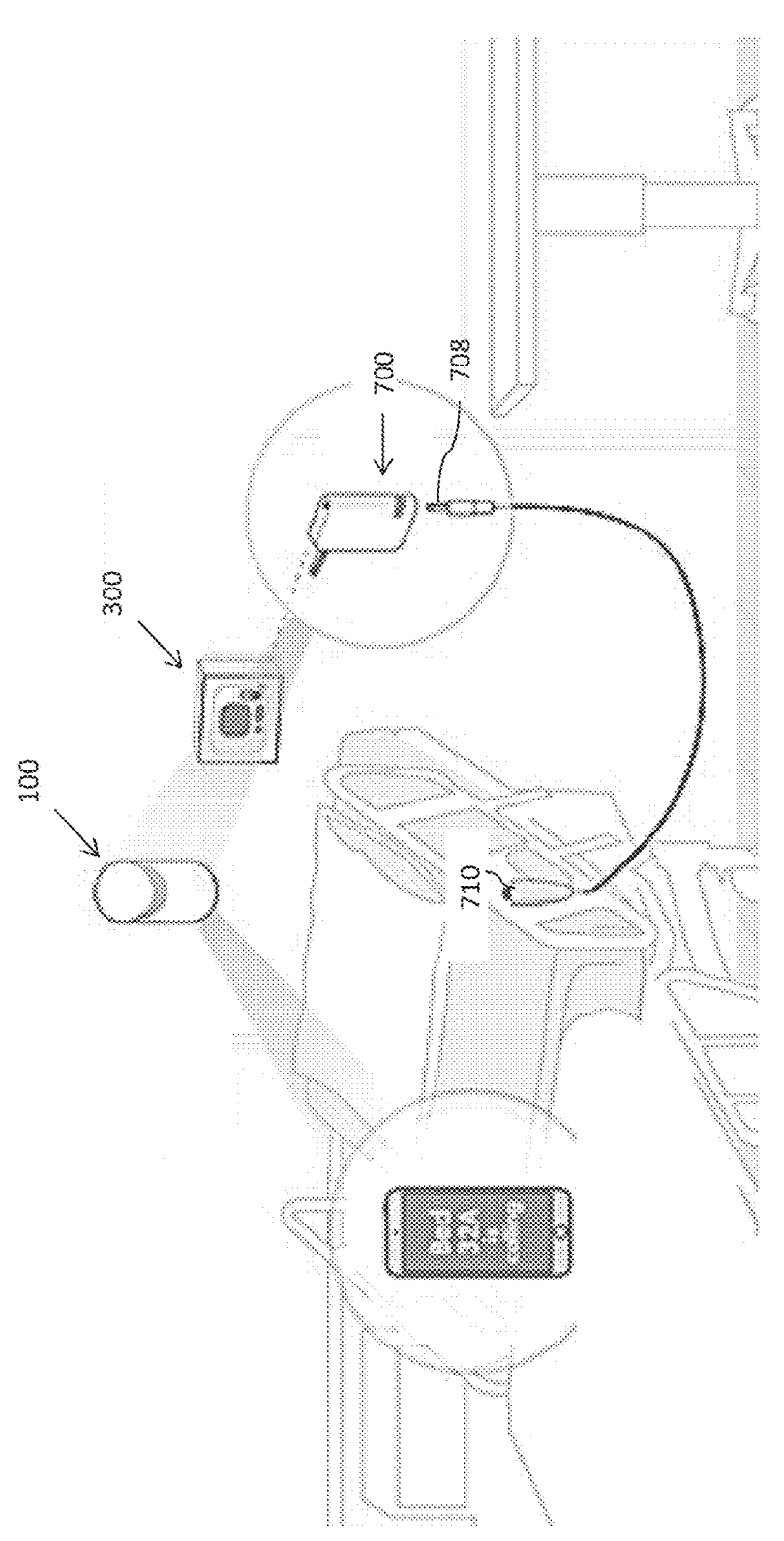
FIG. 21B is a perspective view of a call bell accessory implemented in an existing call bell system.

Referring briefly to FIGS. 21A-21B, there are shown views of a call bell accessory 700, which can be adapted for use with existing call bell systems in healthcare facilities. The depicted call bell accessory 700 is a device with a port 702 for receiving a plug 708 from a call bell button 710 or other call bell actuation mechanism. The call bell accessory 700 also has its own plug 706 adapted for connection to an existing call bell interface 300 (i.e. call bell system) jack or port. The call bell accessory 700 transmits data to the base unit 100 for display on a mobile device application (as explained later). To accomplish this, the call bell accessory 700 detects actuation of the call bell button 710 (or other actuation mechanism) and transmits data indicating the actuation to the base unit 100. The base unit 100 pushes a notification to the mobile device application notifying the user (e.g. assigned nurse, all staff, or nurse station) that a "call bell event" has occurred. Finally, the depicted embodiment of the call bell accessory 700 shown in FIG. 21B includes a light (e.g., LED) display 708, which illuminates when the call bell accessory 700 receives a signal from the call bell button 710 upon actuation.

Figure 22:
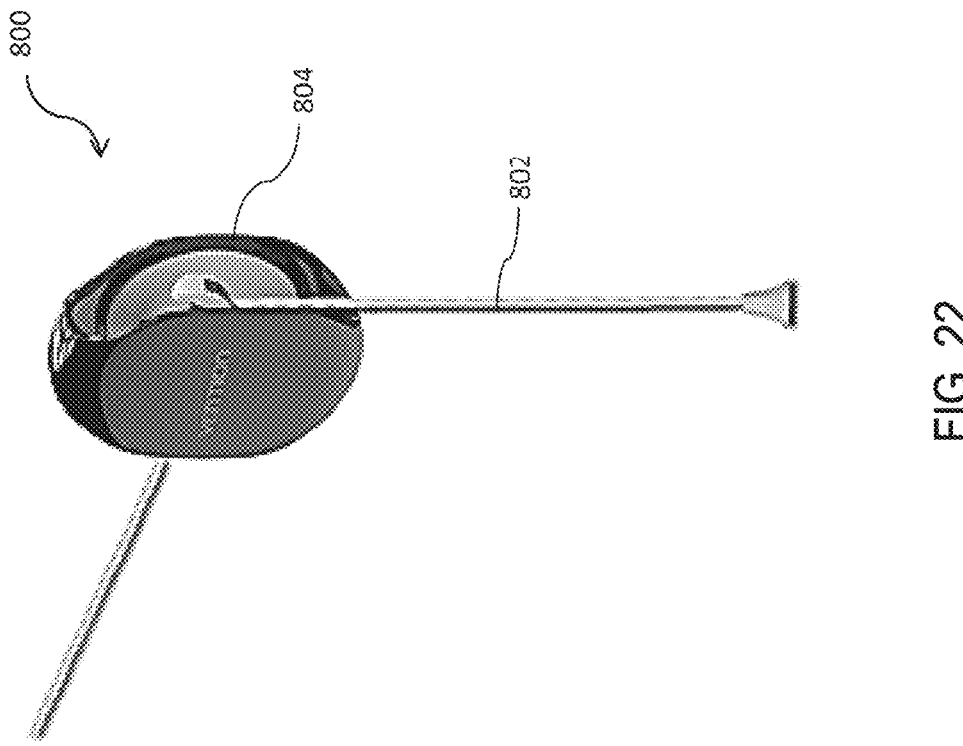
FIG. 22 is a perspective view of a pull-cord system.

In another embodiment, the call bell detector 118 of the base unit 100 may receive a BLE signal from a restroom pull-cord call bell system 800 (hereinafter "pull-cord system"), shown in FIG. 22. The pull-cord system 800 can be adapted to an existing restroom pull-cord. The pull-cord system 800 comprises a BLE-enabled accessory 802, which may receive a pull-cord 804 therethrough. The accessory 802 has a fail-safe pressure switch, which triggers transmission of a BLE signal to the base unit 100 when the pull-cord 804 is pulled. The pull-cord system 800 does not alter any existing restroom pull-cords. For example, the pull-cord 804 may maintain a length required under healthcare regulations, and the pull-cord system 800 may transmit a notification to an assigned nurse or activate a light outside the restroom door. Similar to the call bell accessory 700 described above, the pull-cord system 800 transmits a signal to the base unit 100, which may then push a notification to the mobile device application of a user (e.g., hospital staff or an assigned nurse).

The sensors 112 shown in FIG. 1, may include a microphone, which receives raw audio. The microphone may comprise a sound level detector to get an audio level feature, a speech analyzer to detect if people are talking, and a speech-to-text analyzer to encode spoken words as a feature. The sensors 112 in FIG. 1 may also include ambient light and temperature sensors. The ambient light sensor is digitized to give a light level for the room and the temperature sensor is sampled to give the temperature. These features are published to the feature collector 120 at potentially different rates.

Patients, healthcare providers, and other individuals in the hospital or healthcare facility room also transmit data to the base unit 100 via the beacon detector 108. For example, each healthcare provider may have a wearable beacon 400 that transmits a personal identifier to the beacon detector 108 therefore notifying the positioning system 10 that a particular healthcare provider has entered the room. An illustrative embodiment of a beacon 400 of the positioning system 10 is shown in FIG. 3.

Figure 3:
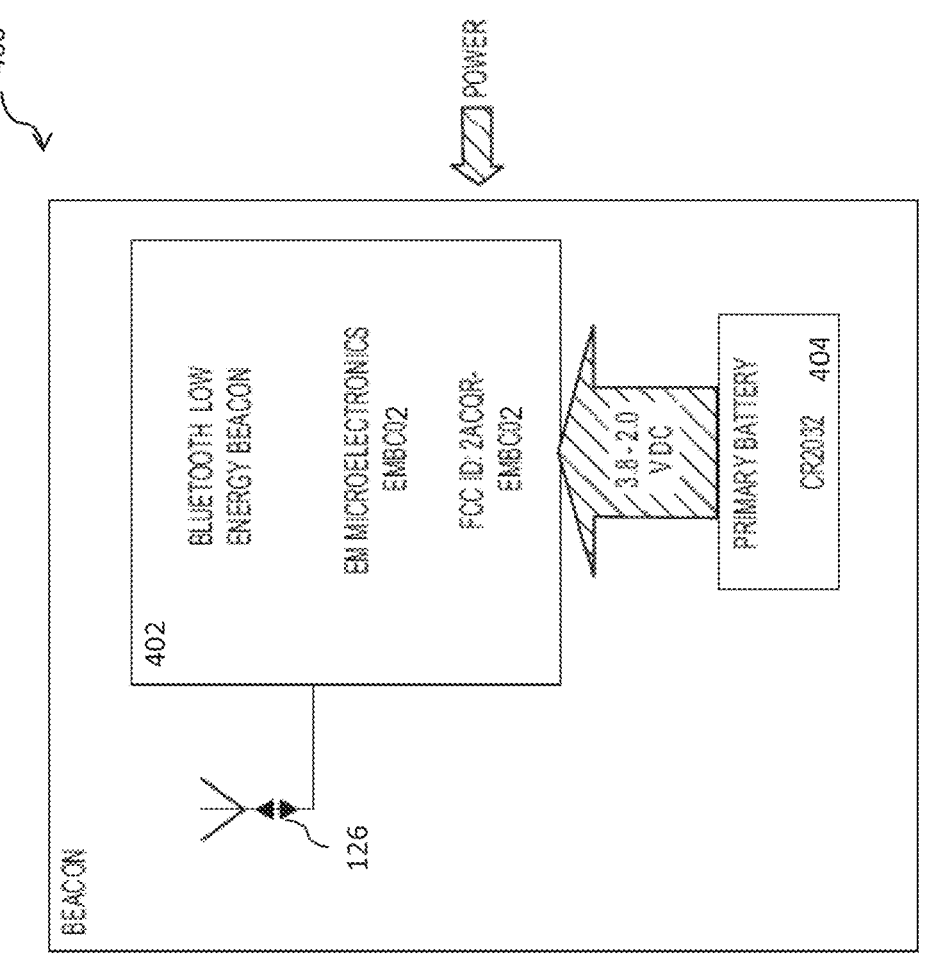
FIG. 3 is a diagram of an illustrative embodiment of a beacon.

Referring now to FIG. 3, the depicted embodiment shows a beacon 400 comprising microelectronics 402 powered by the primary battery 404. The beacon 400 transmits digital data to and, in some instances, receives digital data from the beacon detector 108 shown in FIG. 2. The beacon 400 may take the form of a staff-worn, retractable lanyard, a patient wristband, an embedded module in a device, or a mobile device running an application and configured to broadcast. Each beacon 400 has a BEACON_ID that is readable by the beacon detector 108, which may be associated with a person (e.g., a particular healthcare worker), a role (e.g., nurse), a device (e.g., a spirometer), or an object (e.g., an infusion pump). The beacons 400 also broadcast information other than the BEACON_ID to the beacon detector 108 and ultimately, the microprocessor 402. Such additional information may include accelerometry, button presses, specific function activation, hear rate, heart rate interval, galvanic skin responses, and breathing rate.

Figure 4:
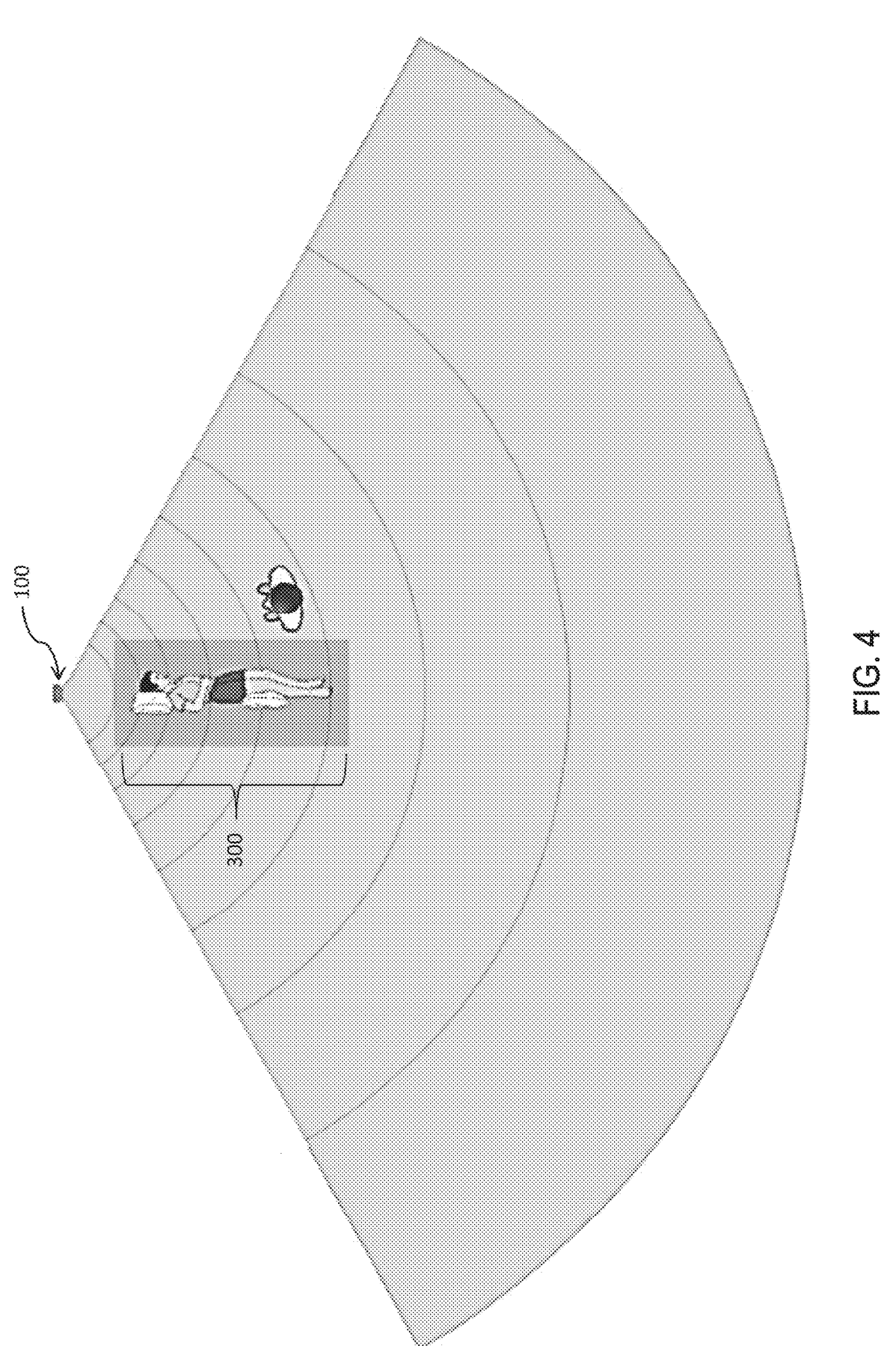
FIG. 4 is a diagram of an illustrative embodiment of the camera field-of-view.

The base unit 100 continuously scans for advertising beacons 400 and publishes received packets with "BEACON_ID", "BEACON_INDICATOR", and "BEACON_ACTIVITY" to the feature collector 120. In one embodiment, the beacons 400 and the beacon detector 108 use Bluetooth Low Energy (BLE) and the base unit 100 is connected to a directional antenna aimed at a patient bed area 300 to detect BLE beacons 400, as shown in FIG. 4. In that embodiment, the BEACON_INDICATOR is the Received Signal Strength Indicator (RSSI) of the broadcasted packet and the BEACON_ACTIVITY is the motion state determined from the accelerometer of the beacon 400, which is encoded in the packet. In alternative embodiments, the beacon detector 108 and the beacons 400 use a different type of communication, such as passive RFID, Zigbee, ultra-wideband, infrared (e.g., IRDA), ultrasound, and light (e.g., with beacons as fiducial markers).

Figure 5:
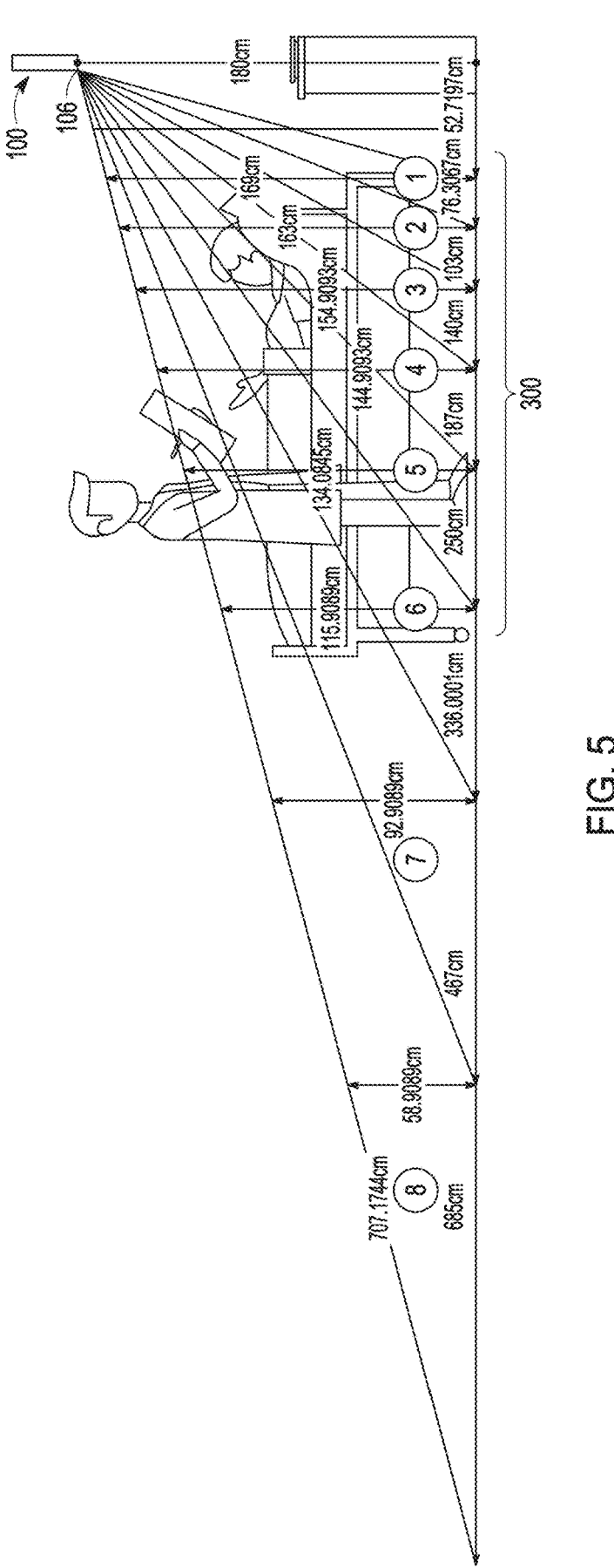
FIG. 5 is a side view of an illustrative embodiment of the camera field-of-view with pixel rows in circles (1-8)
Figure 6:
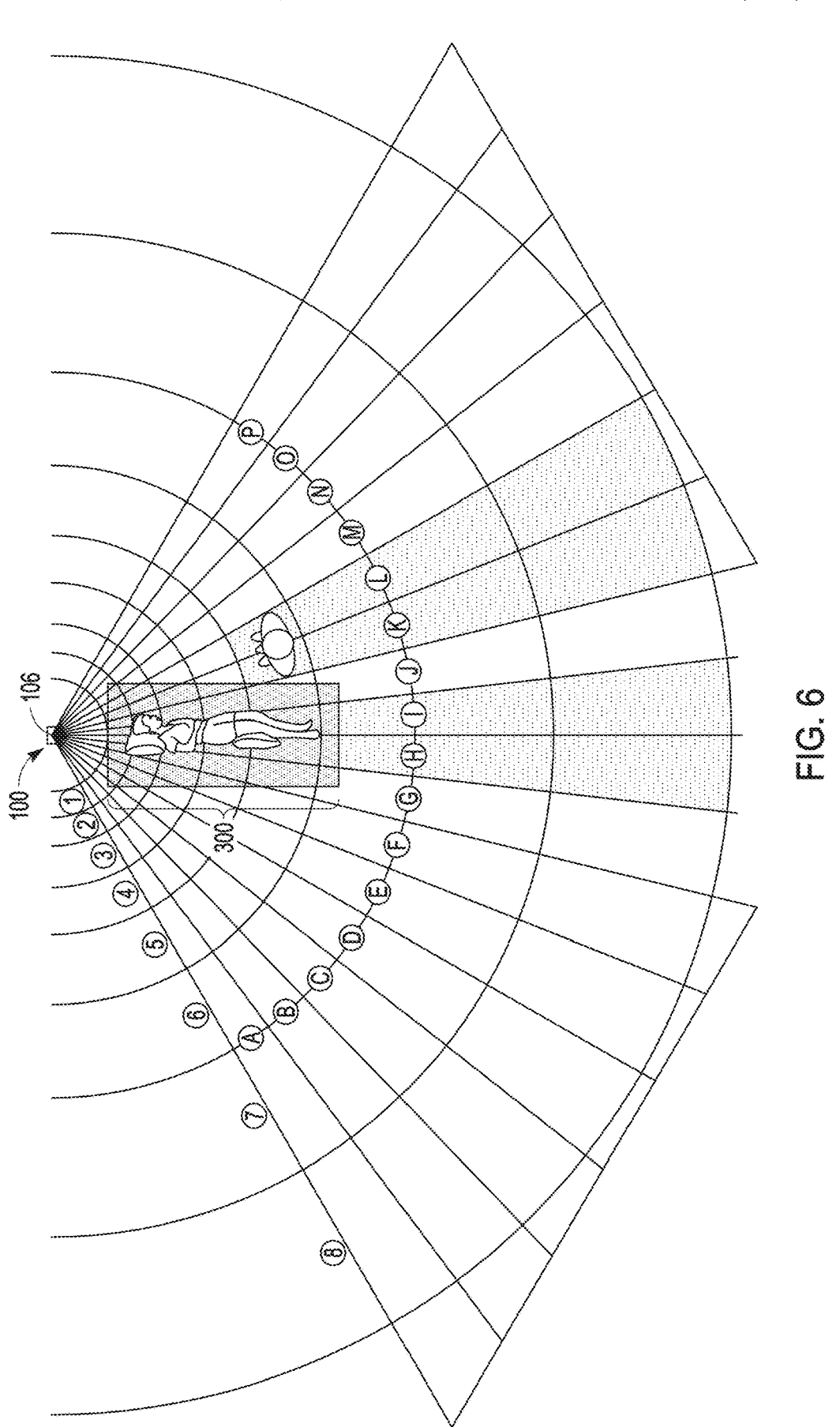
FIG. 6 is a top view of an illustrative embodiment of the camera field-of-view with pixel rows (1-8) and columns (A-P)

Referring now to FIGS. 5-6, there is shown a side view of the camera 106 field-of-view with pixel rows in circles (1-8) in FIG. 5 and a top view of the camera 106 field-of-view with pixel rows (1-8) and columns (A-P) in FIG. 6. In the depicted embodiments, the camera 106 of the base unit 100 is shown on the wall above a patient's bed 300. The camera 106 is angled downward such that the head of the bed to an area past the foot of the bed is in the field-of-view of the camera 106. As subjects and non-subjects enter and exit the field of view of the camera 106, the camera 106 captures images, processes the raw sensor data, and publishes the data to the feature collector 120. In one embodiment, the camera 106 is an array of four Grid-Eye far-field infrared sensors that capture 16 by 16 pixels of temperature information over a 120 degree by 120 degree field of view, up to 10 frames per second. In the same embodiment, 10 frames per second is averaged down to 2 frames per second with output being: 16×16 average, 16×16 variance. In alternative embodiments, the camera 106 is a sensor, such as a stereoscopic IR camera (e.g., Intel RealSense), LIDAR, time of flight, radar, and passive infrared (e.g., motion detector).

Referring back to FIG. 1, the feature collector 120 aggregates and analyzes data received from the detection components of the base unit 100, such as the camera 116, the beacon detector 108, the sensors 112, and the call bell detector 118, for example. The feature collector 120 derives informative, non-redundant values (features) from the data and transmits the features to a scene classifier 202 on the cloud platform 200 and the feature database 504. Referring now to FIGS. 16-19, there are shown flowcharts for the method for detecting and determining the positioning of objects in a room. The depicted embodiment of the method utilizes a beacon (BLE location) algorithm and a camera objection detection (camera location) algorithm. The BLE location algorithm is based on exceeding a threshold to trigger the "enter" (entrance into a room) and a running average falling below the same threshold to trigger the exit (exit from a room). In one embodiment, the camera location algorithm uses the known position and orientation of the camera's field-of-view to infer the radial distance of clusters of pixels from the camera. However, other embodiments and techniques are contemplated, such as those from open source libraries like OpenCV, for example. The embodiment depicted in FIGS. 16-19 is described in terms of input and outputs for the BLE location algorithm and the camera location algorithm.

At a first stage shown in FIG. 16, there is a low level classifier per base unit 100, which may be embedded in the base unit 100 for optimization. For each time step, a BLE location algorithm inputs an array of [Time, BEACON_ID, BEACON_INDICATOR, BEACON_ACTIVITY] and outputs an array of [Time, BEACON_ID, BEACON_INDICATOR, BEACON_ACTIVITY, State: In or Out]. The camera location algorithm inputs an array of [Time, CAMERA_AVGVAL_MATRIX, CAMERA_VARIANCE_MATRIX] and outputs an array of [Time, CAMERA_OBJ_ID, CAMERA_OBJ_COORD {Row 1-8/Column A-P}, CAMERA_OBJ_VARIANCE]. In one embodiment, the algorithm uses the knowledge of the base unit 100 height and camera 106 field-of-view orientation to determine the object coordinates based on the assumption that the objects are people touching the floor if the person is staff member, or on a raised bed if the person is a patient in center of the field-of-view.

At a second stage shown in FIG. 17A-17B, there is a high level classifier per base unit 100, which may also be embedded in the base unit. In one embodiment, shown in FIG. 17A, the BLE location algorithm is constrained by information from the camera location algorithm. First, the BLE location algorithm outputs enter/exits based on transition from out-to-in and in-to-out states. Second, the BLE location algorithm prevents out-to-in transitions when camera location algorithm does not detect a change in the number of objects present. The BLE location algorithm also prevents in-to-out transitions when camera location algorithm does not detect a change in the number of objects present.

Figure 18:
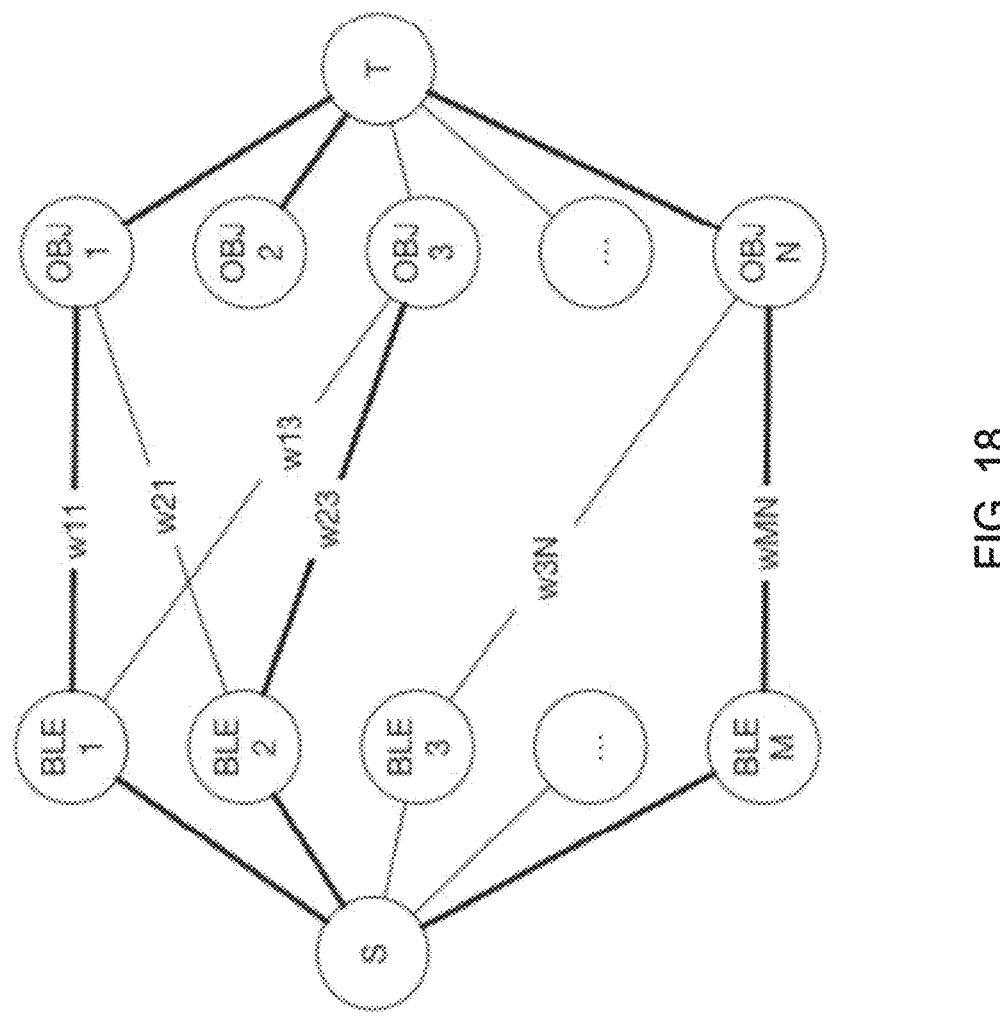
FIG. 18 is an illustrative embodiment of a bipartite graph formulated for the max-flow algorithm.

In an alternative embodiment shown in FIG. 17B, the low level classifiers are fused using graph matching, i.e., the BEACON_ID is matched to the CAMERA_OBJ_ID for each time slice. First, a bipartite graph with BEACON_ID nodes and CAMERA_OBJ_ID nodes is created. Next, a source connects to each BEACON_ID node and a drain connects to each CAMERA_OBJ_ID node. Then, the edges between BEACON_ID and CAMERA_OBJ_ID nodes are weighted based on the "distance" between {BEACON_INDICATOR, BEACON_ACTIVITY} and {CAMERA_OBJ_COORD, CAMERA_OBJ_VARIANCE}. For example, high RSSI and low object row coordinates would be close, where low RSSI and high row coordinates would be close. Also, a "moving" beacon 400 activity state would be close to high camera object variance, and a "stationary" beacon 400 would be close to low camera object variance. Thereafter, all the edges with a weight below an uncertainty cutoff point are pruned. Next, the max-flow algorithm is solved to get a mapping of BEACON_ID to CAMERA_OBJ_ID. An exemplary bipartite graph formulated for the max-flow algorithm is shown in FIG. 18. Finally, for each time step per base unit 100, there is an output array of [Time, BEACON_ID, BEACON_INDICATOR, BEACON_ACTIVITY, CAMERA_OBJ_ID, CAMBERA_OBJ_COORD, CAMERA_OBJ_VARIANCE, CONFIDENCE_VALUE], where the CONFIDENCE_VALUE is derived from the "distance" of the match.

According to another embodiment, the low level classifiers are fused using probabilistic graphical model. A neural network is used to perform multi-modal sensor fusion with an input of [Beacon, Camera] and an output of [known coordinates as measured from reference system]. At the conclusion of the second stage, in all of the embodiments described above, the system 10 outputs an array of [Time, BEACON_ID, State: In or Out, Activity: Moving or Stationary, Coordinate, Confidence Value 0-1] for each base unit 100 (shown in FIG. 19).

Figure 19:
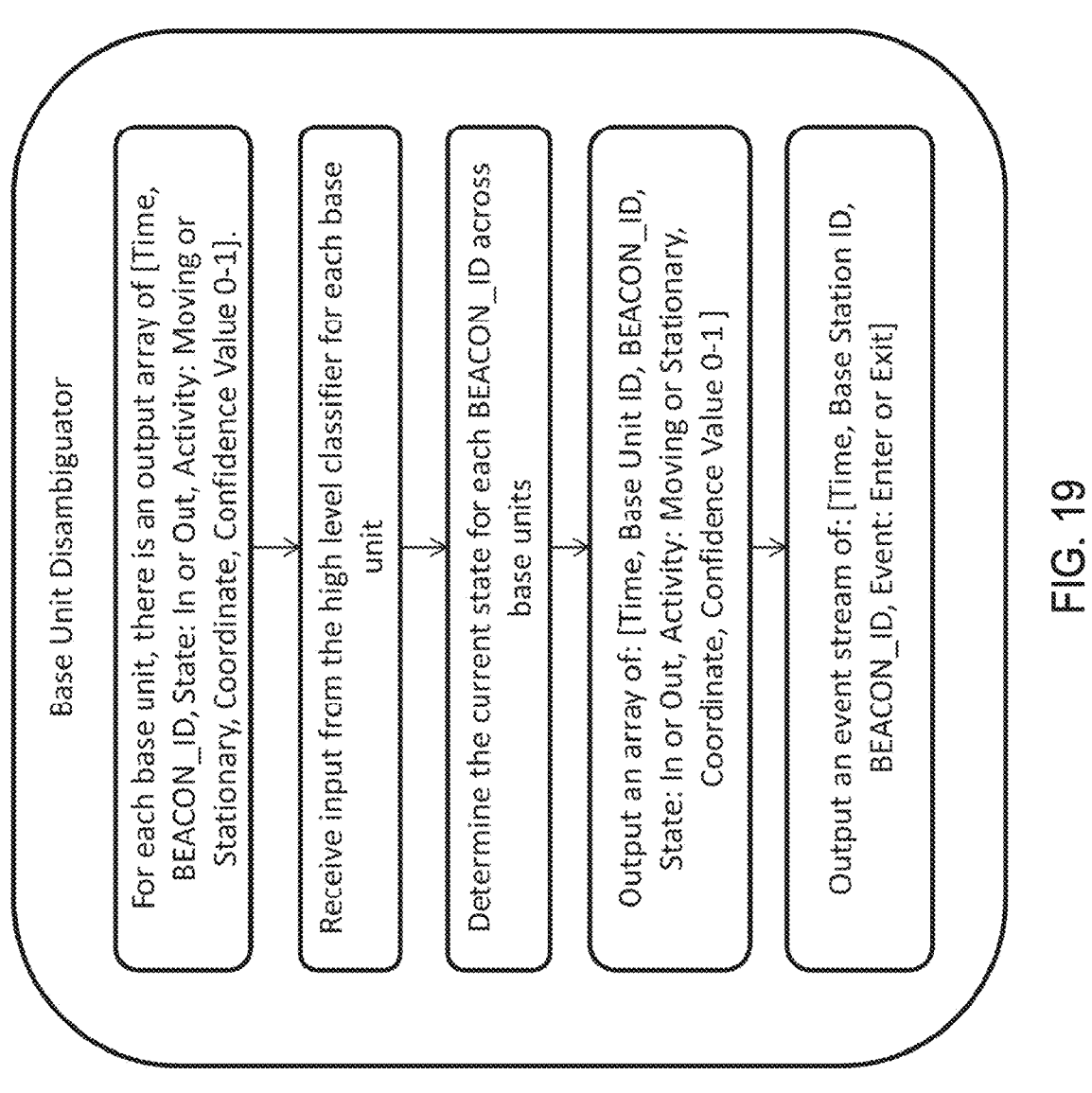
FIG. 19 is a flowchart of an illustrative embodiment of a method for base state disambiguation.

At the third stage, the cloud platform 200 connected to the base unit 100 disambiguates input from the high level classifier for each base unit 100, as shown in FIG. 19. Here, a current state for each BEACON_ID across all base units 100 is determined. In one embodiment, the system 10 may transition a BEACON_ID to new "in" states if they occur at a configurable number of seconds. In another embodiment, the system 10 may choose a base unit 100 with a higher confidence value, if available, for "in" state. In another embodiment, the system may use a probabilistic model such as a Hidden Markov model to determine the current in or out state of a BEACON_ID at each base unit using a configurable number of historical states with the model with the maximum posterior likelihood across all base units being determined to be correct. Next, the output is an array of [Time, Base Unit ID, BEACON_ID, State: In or Out, Activity: Moving or Stationary, Coordinate, Confidence Value 0-1 and the event stream of [Time, Base Station ID, BEACON_ID, Event: Enter or Exit].

Figure 20:
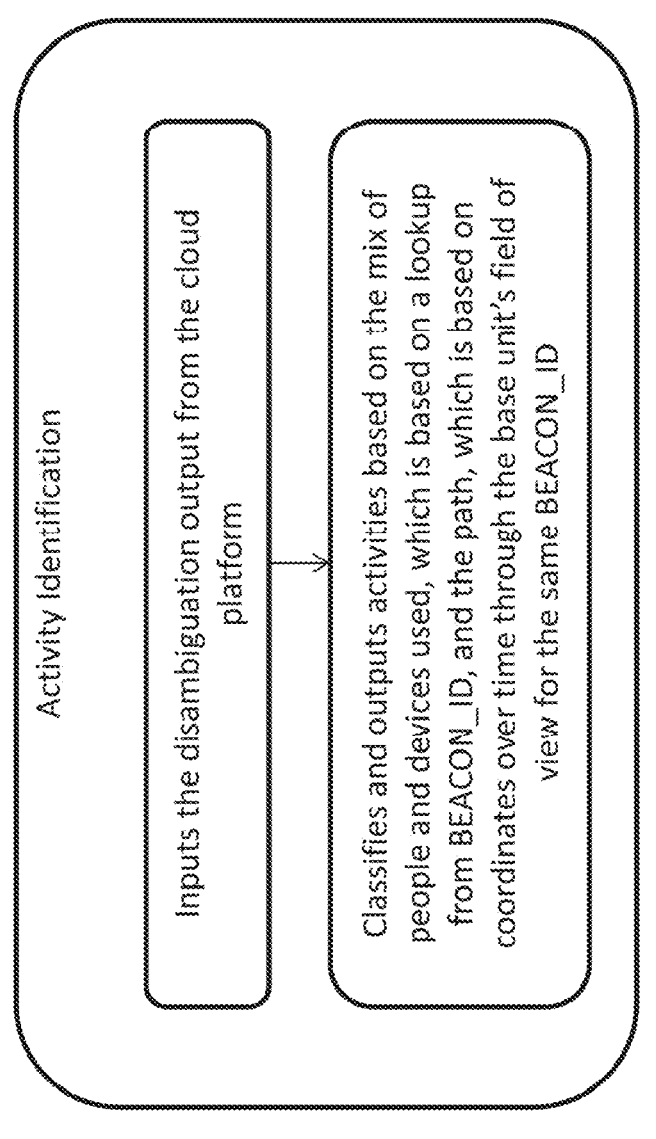
FIG. 20 is a flowchart of an illustrative embodiment of a method for activity identification.

At the final stage, there is activity identification, as shown in FIG. 20. The system 10 inputs the disambiguation output from the cloud platform 200. The system 10 then classifies and outputs activities based on the mix of people and devices used, which is based on a lookup from BEACON_ID, and the path, which is based on coordinates over time through the base unit 100's field of view for the same BEACON_ID. Such activities include staff activity, patient activity, and patient with staff activity. For example, staff activity may include hourly rounding, bedside reporting, and grand rounds. Patient activity may include activities such as using a spirometer, ambulating, and lying in bed. In another example, patient with staff activity may include instances where healthcare providers are interacting with patients, such as rotating the patient for pressure ulcers, assisting patients with restroom use, and feeding the patient.

Referring back to FIG. 1, the feedback engine 122 subscribes to the scene classifier 202 and publishes commands to the display 114 or speaker 116 when location events and/or activities occur (or do not occur). Such location events and/or activities may correspond to feedback rules 124, which signal the feedback engine 122 to publish commands. The location events and/or activities may occur when the patient has not been visited recently, a rounding goal has not been satisfied, a bedside reporting goal has not been met, a patient is in danger of falling, a patient has requested help, staff is present after a patient requested help, and a patient has not been rotated or turned, for example. When a command publishes from the feedback engine 122 to the display 114, the command may manifest as a color pattern. For example, if the patient has not been visited recently, the display 114 may show an orange light pattern or if a rounding goal has not been satisfied, the display 114 may show a green light pattern. As the display 114 is integrated into the front housing of the base unit 100, the commands (i.e., light patterns) may be seen by healthcare providers, alerting them of a patient's current status. As previously stated, the commands may also be published to a speaker 116.

From the scene classifier 202, the activities are analyzed in an analytics module 206 using algorithms stored in the analytics database 208. Exemplary key metrics that are calculated in the analytics module include the frequency of visits, the duration of visits, an hourly rounding rate, a bedside reporting rate, a patient turning rate, and patient ambulation rate. These key metrics can be broken down and calculated for each staff role, patient, unit, department, day of the week, or time of day. After analysis, the resulting data is transmitted to the reporting API module 210, which uses a publish-subscribe mechanism such as MQTT, for example, where data from a reporting database 212 determines how the data will be reported to a mobile application 214 or web application 216. Once the data is transmitted to a mobile application 214 or web application 216, such as a restful HTTP interface, a user can view the data at the interface.

Still referring to FIG. 1, the cloud platform 200 also comprises a scene classifier trainer 500. The scene classifier trainer 500 comprises a label database 502 and a feature database 504. Feature data is recorded to the feature database 504 in a more highly compressed state than raw signal data to remove certain privacy concerns. Labeled data stored in the label database 502 includes manually observed information 600b, such as system trainer entries and patient feedback entries. Labeled data also comprises electronic record data 600a, such as electronic medical records (EMR), electronic healthcare records (EHR), hospital information systems (HIS), unstructured notes made by staff, workflow data entered by staff, and coding done by hospital billing specialists. Finally, labeled data may also include any device-generated data, such as data from medical devices.

The scene classifier trainer 500 then uses data from the label database 502 and the feature database 504 in model training 506 to create and store scene models 508. A scene model may include topic models, such as hierarchical latent Dirichlet allocation (LDA), Hidden Markov models, and neural networks. Model training 506 includes machine learning methods, such as back propagation, feed forward propagation, gradient descent, and deep learning. Therefore, future features from the feature extractor 120 may be more quickly classified into the appropriate scene using a scene model 508 created using the same or similar past features.

Figure 7B:
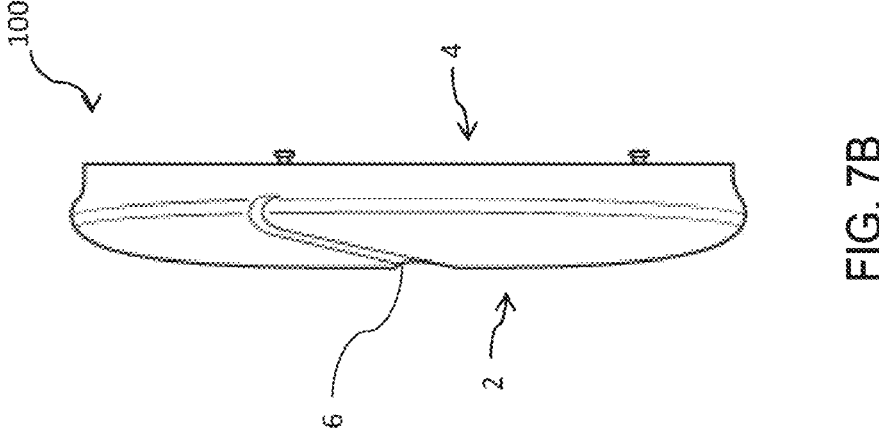
FIG. 7B is a side perspective view of an illustrative embodiment of the base unit.
Figure 7A:
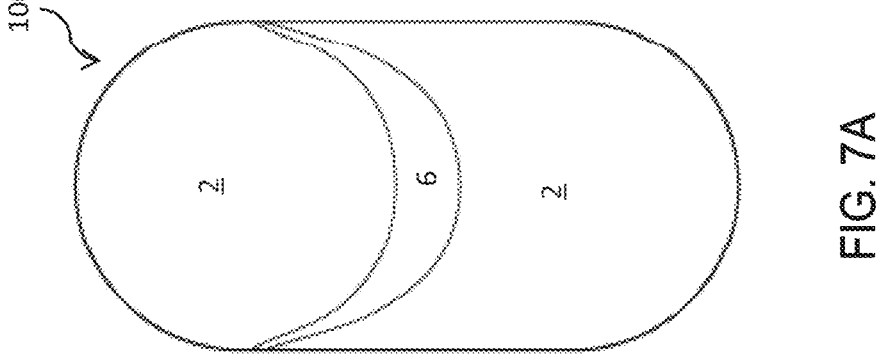
FIG. 7A is a front perspective view of an illustrative embodiment of the base unit.
Figures 7C, 7D:
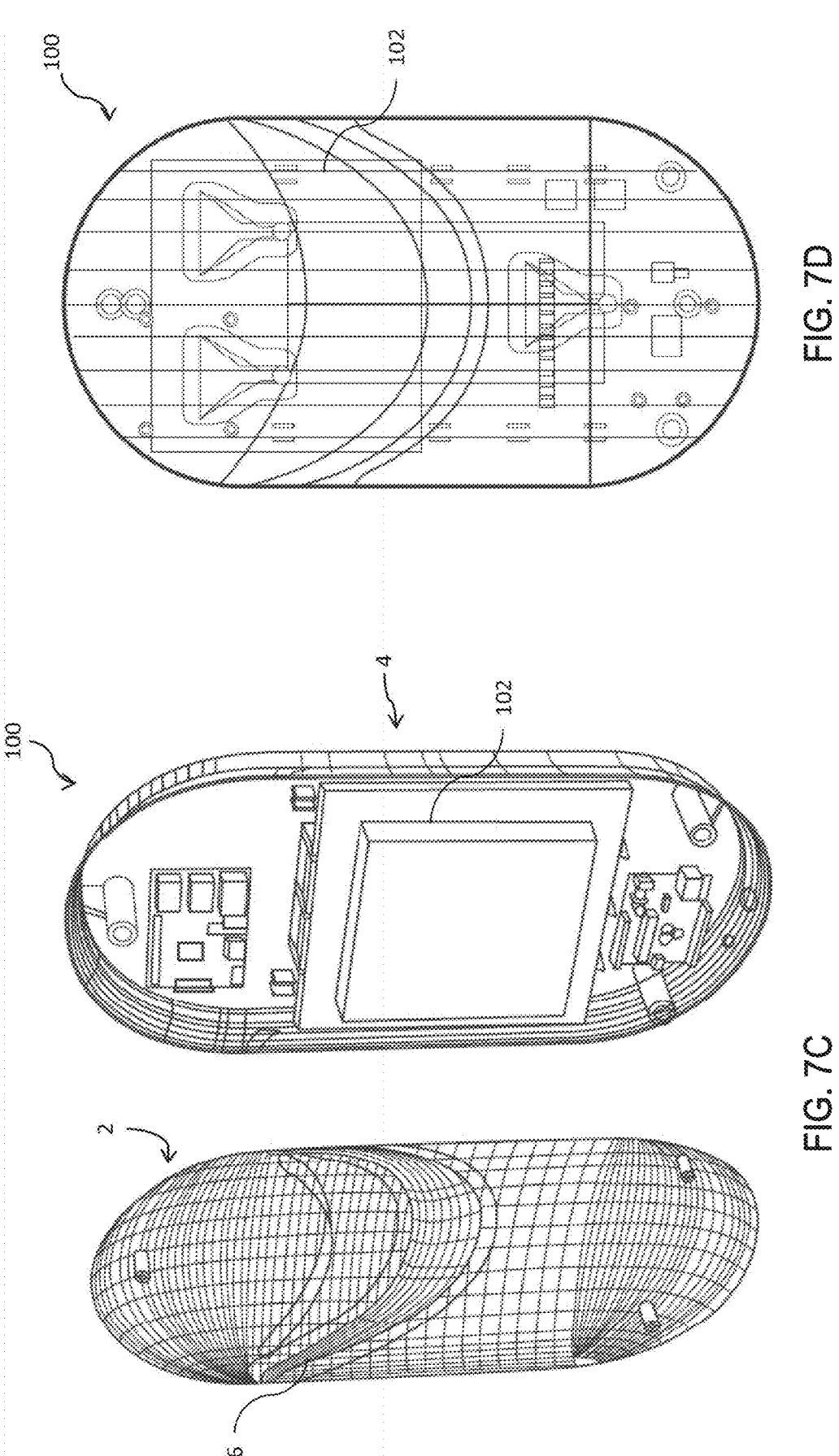
FIG. 7C is a perspective view of an illustrative embodiment of the interior of the base unit.
FIG. 7D is a perspective view of an illustrative embodiment of the internal components of the base unit.

With reference to FIGS. 7A-11D, perspective views of the base unit 100 and skeletal models derived from the positioning system 10 are shown. Referring first to FIGS. 7A-7B, there is shown a front perspective view of the base unit and a side perspective view of the base unit 100, respectively. In the depicted embodiment, the base unit 100 is stadium-shaped with a curved first surface 2 and a flat second surface 4. The first surface 2 comprises a crescent shaped aperture 6. A camera, such as a Panasonic Grid-Eye, is connected within the front-bottom area of the base unit 100, such that the field-of-view extends outward from the base unit 100 to the environment. Referring now to FIGS. 7C-7D, there are shown perspective views of illustrative embodiments of the interior of the base unit 100 and of the internal components of the base unit 100, respectively. FIGS. 7C-7D shows the crescent shaped aperture 6 for the LED display 114, BLE transceiver 108, camera 106, microprocessor 102, and the sensors 112 of the base unit 100. The base unit 100 is shown mounted on a wall above a patient bed or other designated patient area. The base unit 100 only needs power and a Wi-Fi connection to operate.

Figure 8:
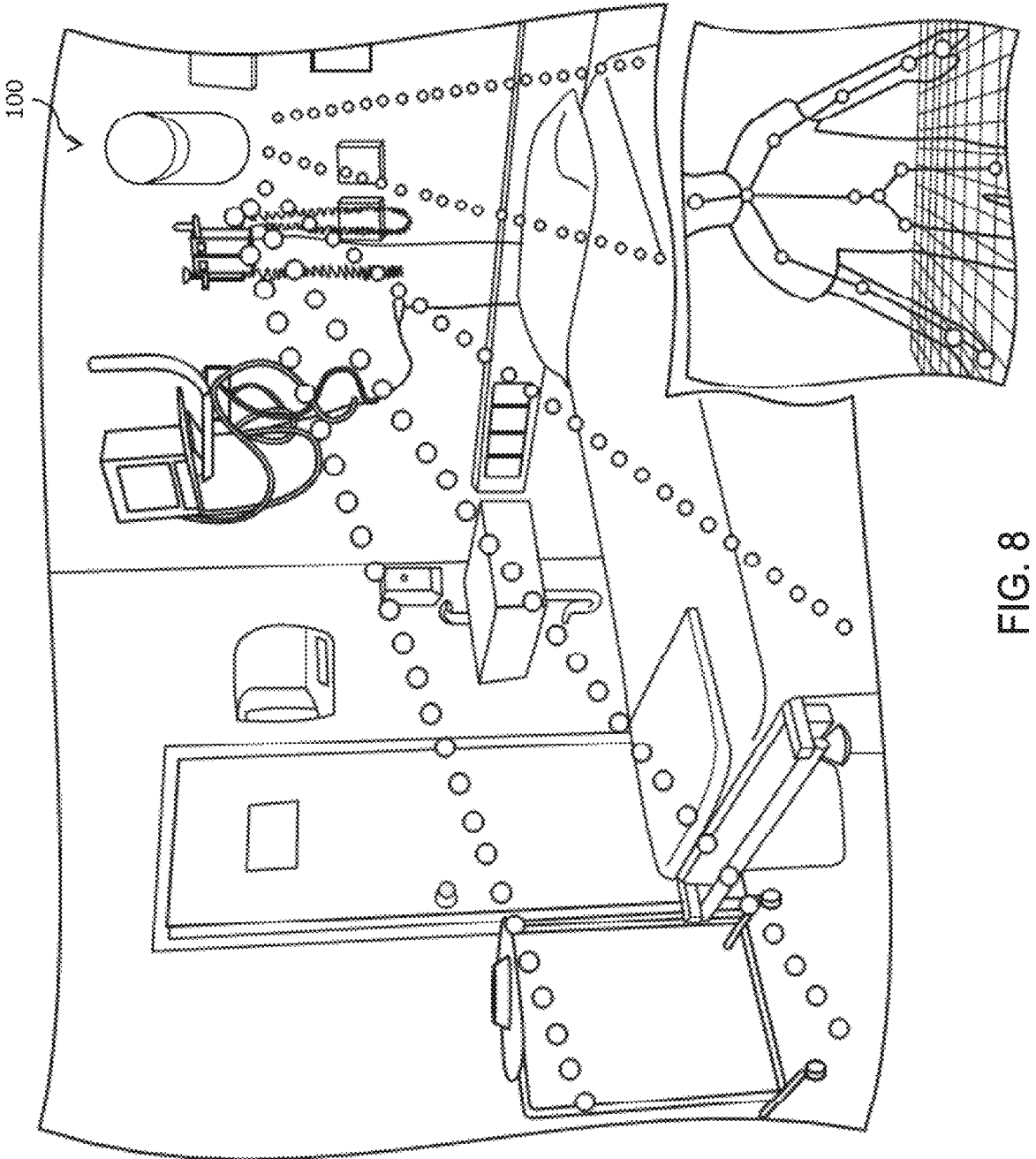
FIG. 8 is a perspective view of an illustrative embodiment of the base unit on a hospital room wall.
Figure 9:
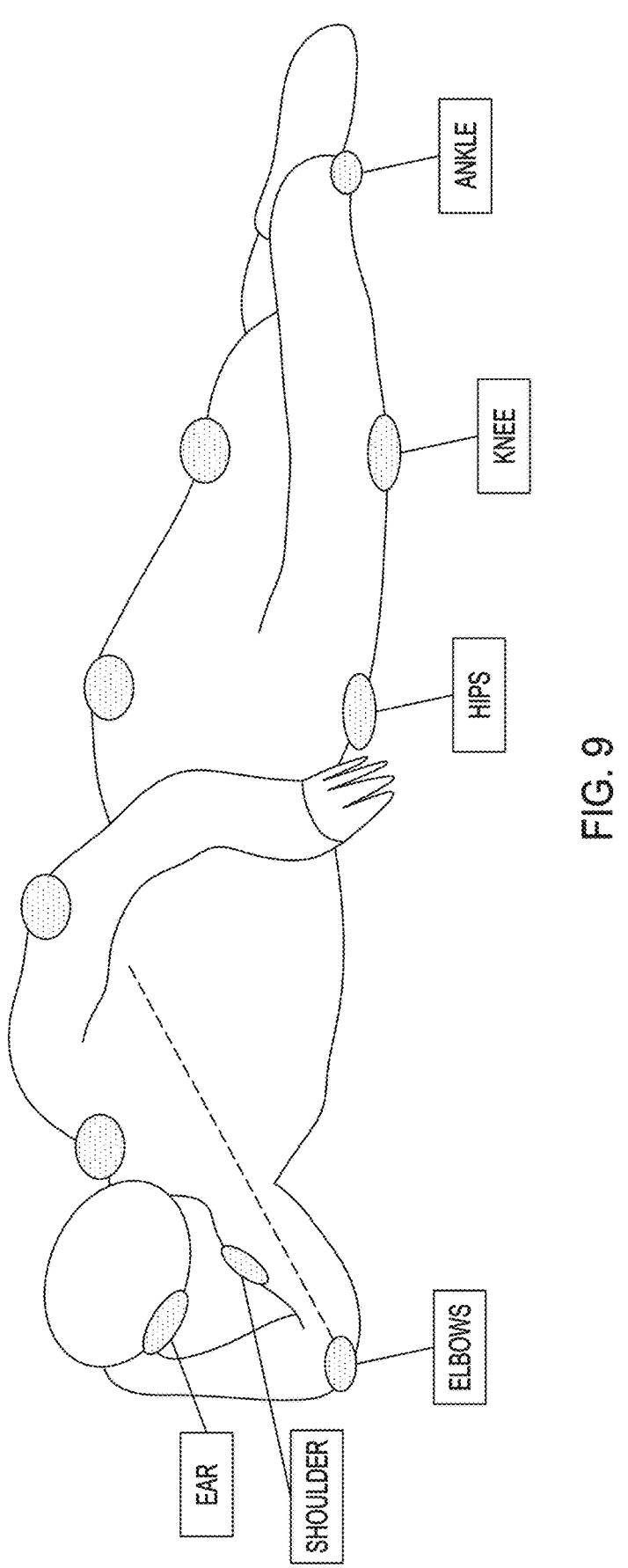
FIG. 9 is a diagram of an illustrative embodiment of exemplary joint locations used to create a skeletal profile.

In one embodiment, all functionalities of the base unit 100 are controlled via Bluetooth through an authorized smartphone device or other mobile device. Such components eliminate the need to touch the base unit 100 directly, which is critical for a device that is mounted to hospital and healthcare facility walls, as shown in FIG. 8. The base unit 100 is also easy to clean as the surfaces 2, 4 are substantially seamless, with the exception of the aperture 6.

Referring again to FIG. 8, the positioning system 10 uses the camera 106 to create a field-of-view of detection surrounding the patient's bed where the majority of care takes place. The system 10 uses algorithms in the analytics database 208 (of FIG. 1) based on skeletal joints, such as those shown in FIG. 9, to create a skeletal profile in 3 mm intervals for accurate identification and monitoring of patients who cannot re-position themselves. Real-time analysis of patient positioning while in the bed is critical to assessing the patient's risk of developing a hospital acquired pressure ulcer (HAPU) if patient not repositioned in a 2 hour time frame. The skeletal profile also provides more appropriate determinations of the need and subsequent management of patients in restraints, patients who have 1:1 care, patients with seizures, as well as the analysis of more complex movement disorders and complex patient movements.

Figure 10B:
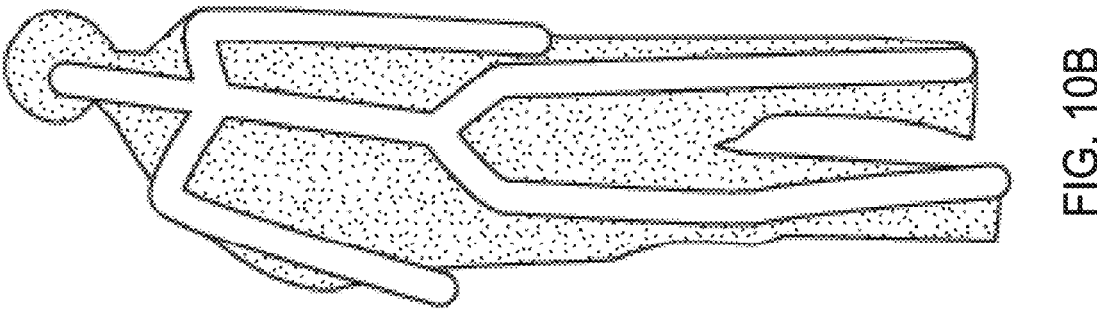
FIG. 10B is a diagram of an alternative illustrative embodiment of a skeletal ambulatory profile.
Figure 10A:
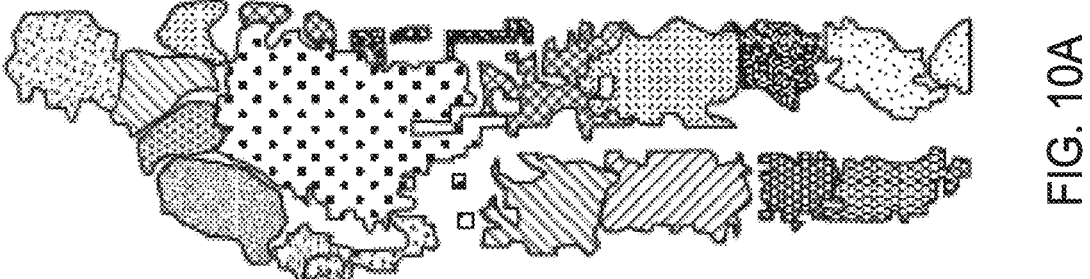
FIG. 10A is a diagram of an illustrative embodiment of a skeletal ambulatory profile.

By capturing only the outline of an individual, the positioning system drastically reduces processing capacity. Further, the analytics database 208 (of FIG. 1) may also store gait analysis algorithms to create a skeletal ambulatory profile of a patient, such as shown in FIGS. 10A-10B. Gait analysis can establish a patient's fall risk as well as aid in tracking rehabilitation progress. Real-time alerting in the event of a patient fall based on the analysis of skeletal positioning and relationship to the ground allows for quick staff response times and better care for the patient.

Figure 11B:
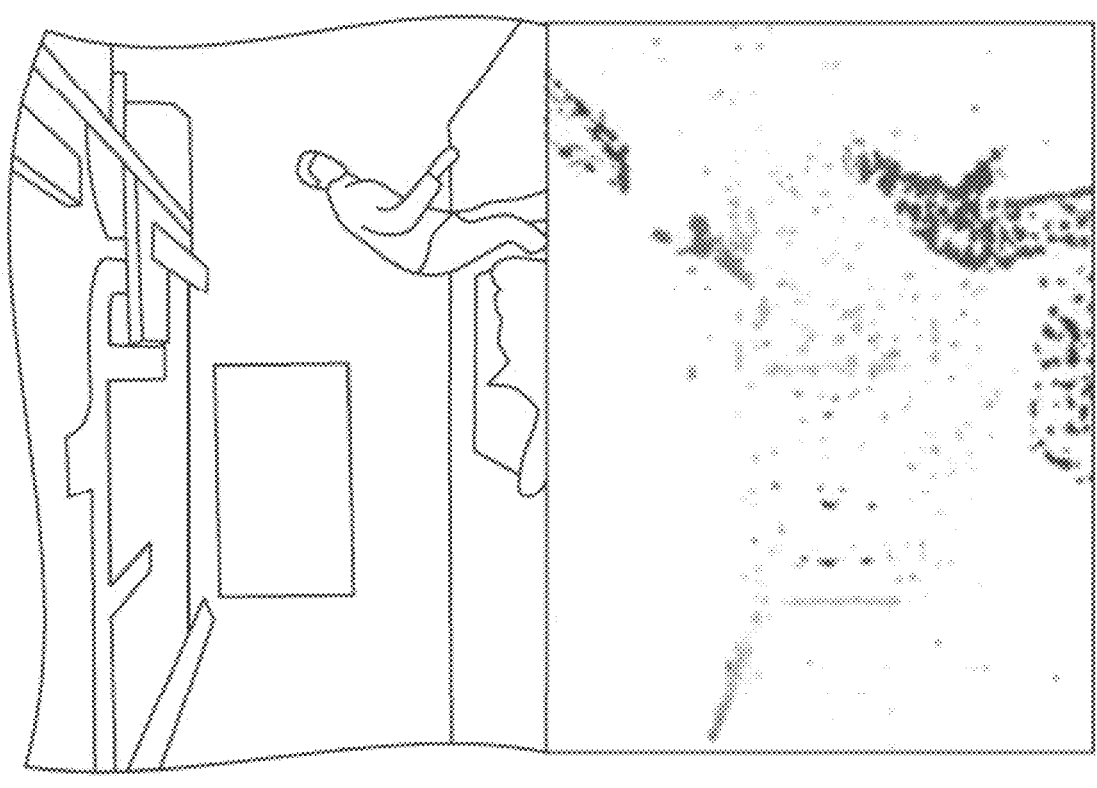
FIG. 11B is another side-by-side comparative diagram of a patient action and the corresponding skeletal profile.
Figure 11A:
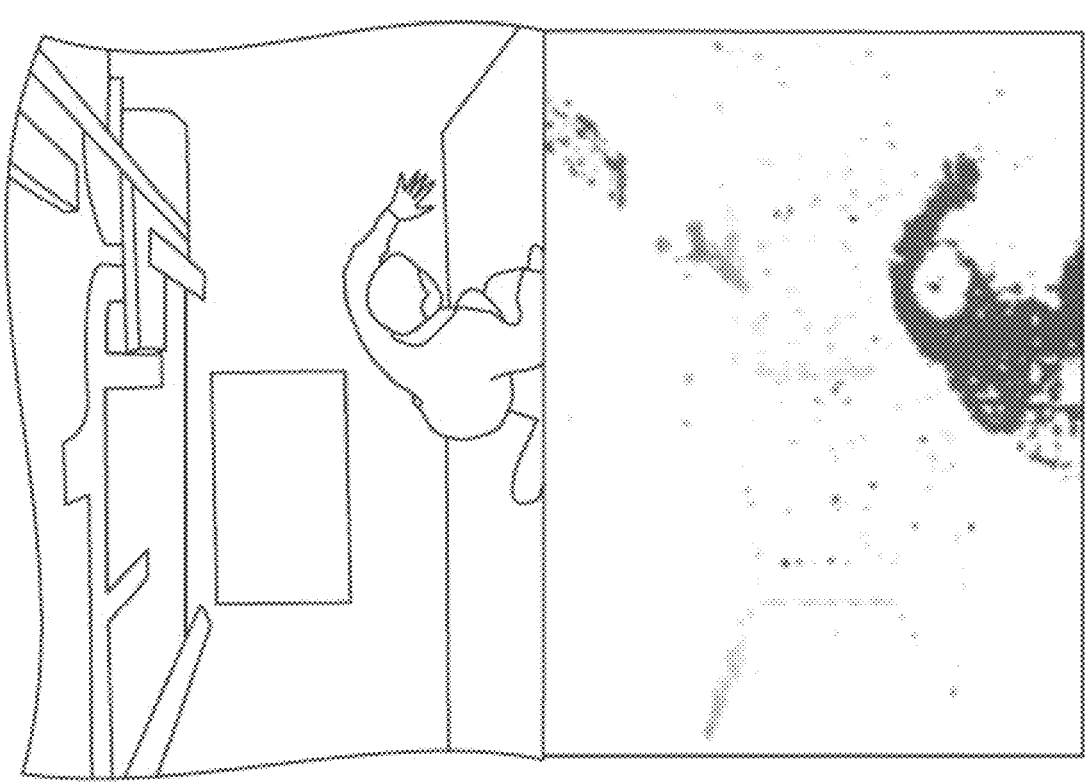
FIG. 11A is a side-by-side comparative diagram of a patient action and the corresponding skeletal profile.
Figure 11D:
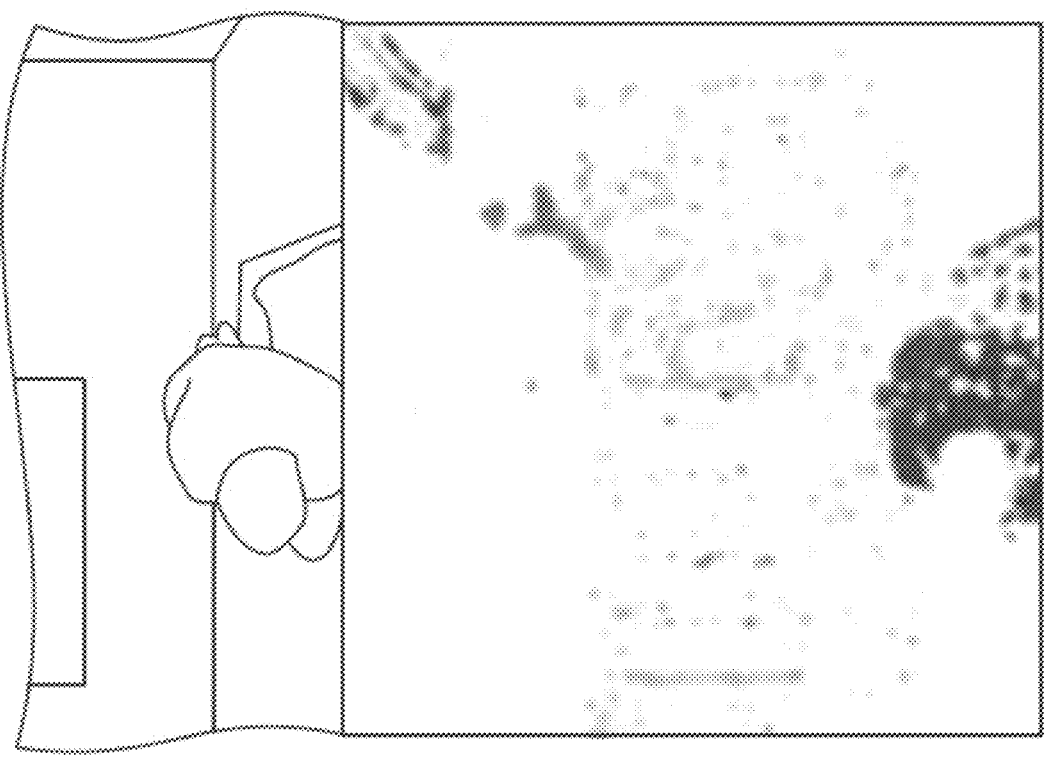
FIG. 11D is another side-by-side comparative diagram of a patient action and the corresponding skeletal profile.
Figure 11C:
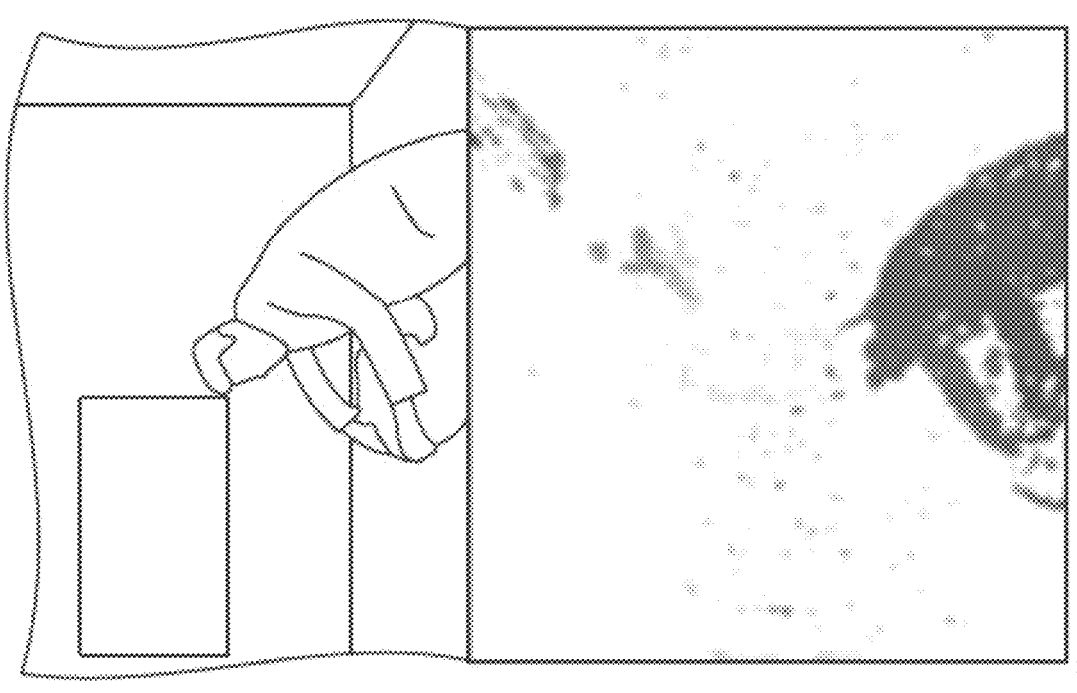
FIG. 11C is a side-by-side comparative diagram of a healthcare provider action and the corresponding skeletal profile.

FIGS. 11A-11D provide side-by-side comparative diagrams of either a patient or healthcare provider action and the corresponding skeletal profile. The term "skeletal profile" used with reference to FIGS. 11A-11D can be any body image produced alone or in combination through joint movement tracking, gesture tracking, thermal imaging, and other body mechanic recognition. FIG. 11A shows a patient getting out of bed without supervision and FIG. 11B depicts the patient standing unsupervised. The patient in FIG. 11B can be analyzed using the positioning system, such as through the patient gait analysis, which provides a fall risk for the patient. FIGS. 11C-11D depict a patient incapable of repositioning himself. In FIG. 11C, the patient is turned by the healthcare provider to prevent pressure ulcers. Using a skeletal profile of the patient, it can be determined if the patient is turned within the recommended time frame to prevent pressure ulcers.

Figure 12C:
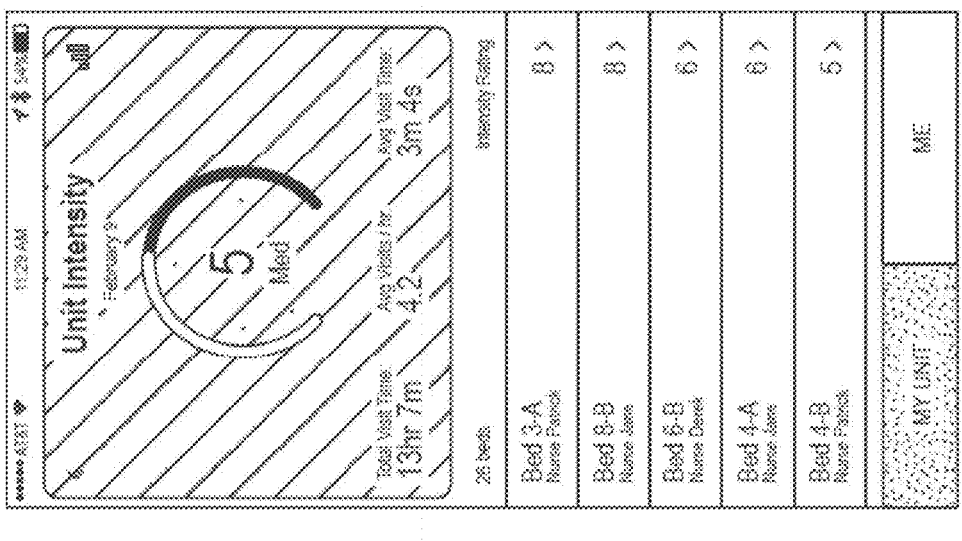
FIG. 12C is a perspective view of an illustrative embodiment of a Unit Intensity analysis interface for the positioning system.
Figure 12B:
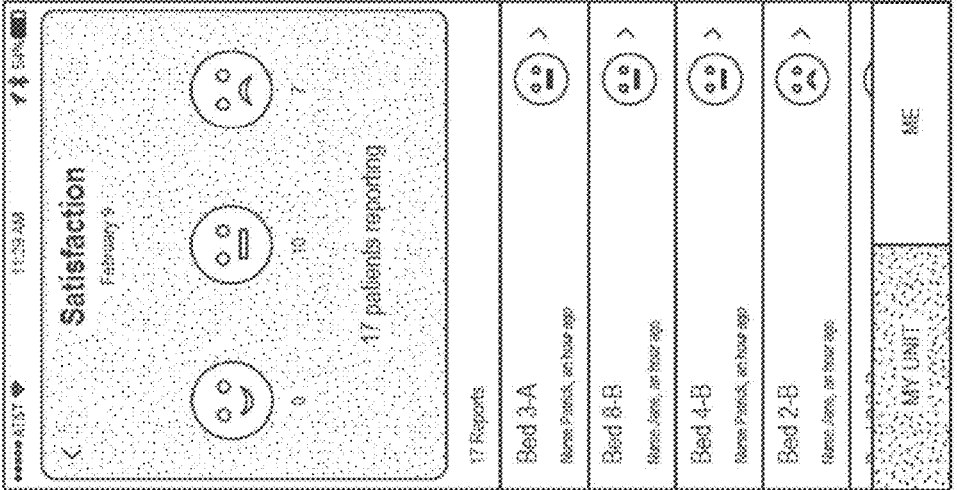
FIG. 12B is a perspective view of an illustrative embodiment of a Patient Feedback analysis interface.
Figure 12A:
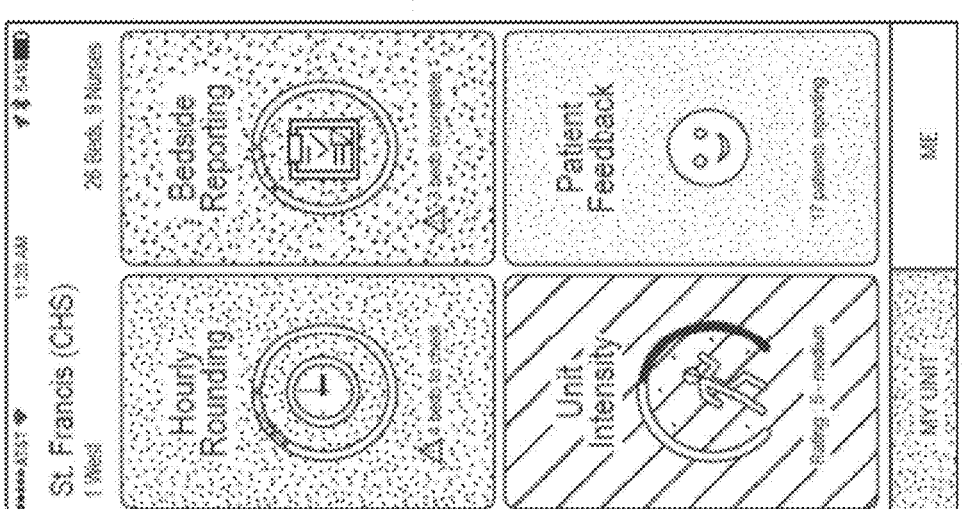
FIG. 12A is a perspective view of an illustrative embodiment of a healthcare management main screen interface for the positioning system.

The cloud platform provides a pathway to push data to users' mobile devices. With reference to FIGS. 12A-15, there are shown perspective views of illustrative embodiments of mobile application interfaces of the positioning system. First, FIG. 12A shows an illustrative embodiment of a healthcare management main screen interface. In the depicted embodiment, the main screen interface shows information such as the hospital name ("St. Francis (CHS)"), number of beds ("26 Beds"), number of healthcare providers on duty ("9 Nurses"), and the location in the hospital ("1 West"). The main screen also shows four options for analyses modules: "Hourly Rounding," "Bedside Reporting," "Unit Intensity," and "Patient Feedback." FIG. 12B shows an illustrative embodiment of the "Patient Feedback" analysis interface. The application provides information such as the number of patients providing feedback ("17 patients reporting"), with the feedback summarized and listed according to patient bed number. In FIG. 12C, there is shown an illustrative embodiment of the "Unit Intensity" analysis interface. The system quantifies unit intensity for the entire healthcare practice, such as a hospital or long-term care facility, or a subdivision thereof. The depicted embodiment shows the unit intensity calculated based on the total time that all healthcare providers in the unit, such as nurses, spent with patients, the average time spent visiting patients per hour, and the average time spent visiting each patient. Finally, the Unit Intensity analysis interface not only displays an intensity rating for the unit, but also displays an intensity rating for each individual healthcare provider (nurse).

In FIG. 13A, there is shown an illustrative embodiment of the "Hourly Rounding" analysis interface. The Hourly Rounding analysis interface provides information such as the total number of rounds (patient visits) completed, the number of beds that are past due to be checked, and if there is an upcoming bed due to be checked soon. The application interface also shows the bed number of each bed to be checked and the time elapsed since the last check. Referring now to FIGS. 13B-13C, there are shown two embodiments of hourly rounding history interfaces, one with hourly rounding analyzed by week and the other with hourly rounding analyzed by day for the current week. FIG. 13B shows the hourly rounding history analyzed by week, with a compliance percentage for each week. FIG. 12C shows the hourly rounding history for each day of the week, shown as a compliance percentage.

Figure 14C:
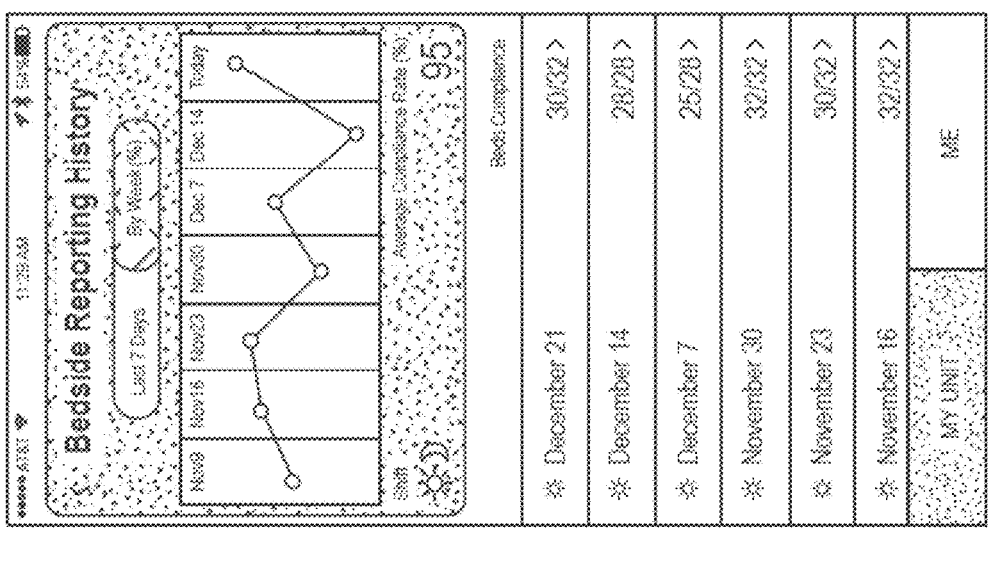
FIG. 14C is a perspective view of an illustrative embodiment of Bedside Reporting History interface.
Figure 14B:
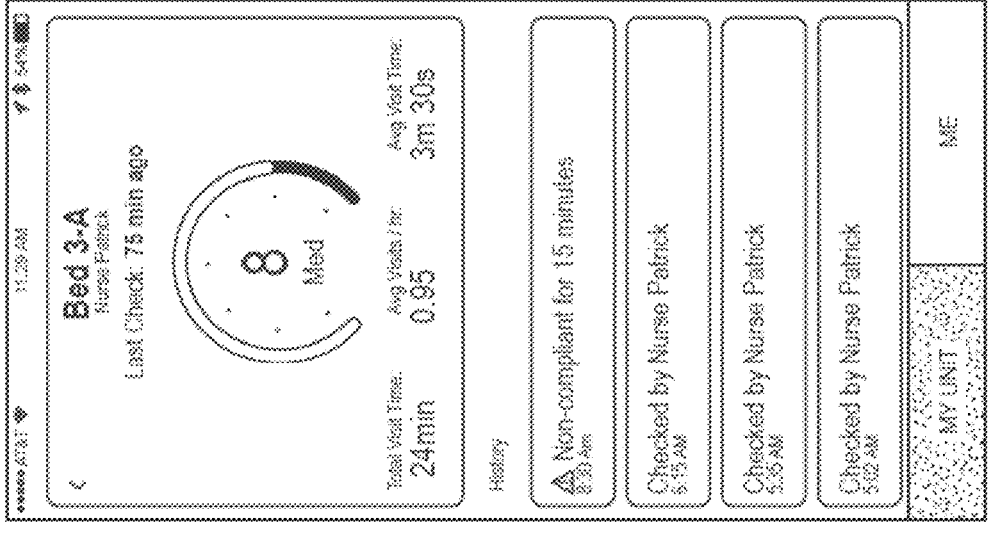
FIG. 14B is a perspective view of an illustrative embodiment of a Bedside Reporting analysis interface for a particular bed number.
Figure 14A:
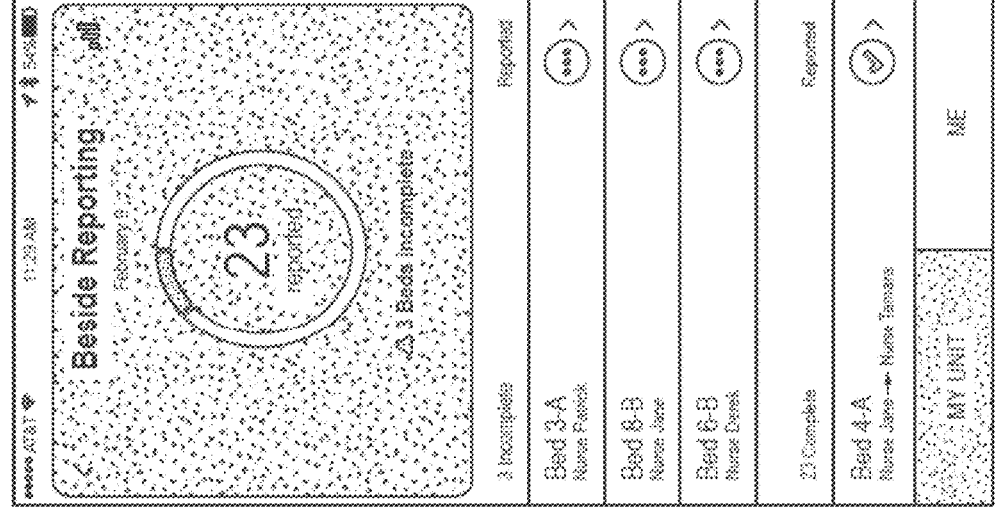
FIG. 14A is a perspective view of an illustrative embodiment of a Bedside Reporting analysis interface.

Referring now to FIGS. 14A-14C, there are shown illustrative embodiments of the "Bedside Reporting" analysis interface. As shown in FIG. 14A, the "Bedside Reporting" interface provides information such as the number of bedside checks that have been reported and the healthcare provider (nurse) that reported a bedside check. As shown in FIG. 14B, the Bedside Reporting interface can also display the history of bedside checks for that particular bed and the healthcare provider (nurse) who performed each listed beside check. The display also shows whether the bed needs to be checked and is past the compliance time window. Similar to the "Unit Intensity" interface, the "Bedside Reporting" interface shown in FIG. 14B also provides an analysis of the total time spent at a particular bed, the average time per visit, and the average duration of the visit. FIG. 14C shows the bedside reporting history analyzed by week, with a compliance percentage for each week.

Figure 15:
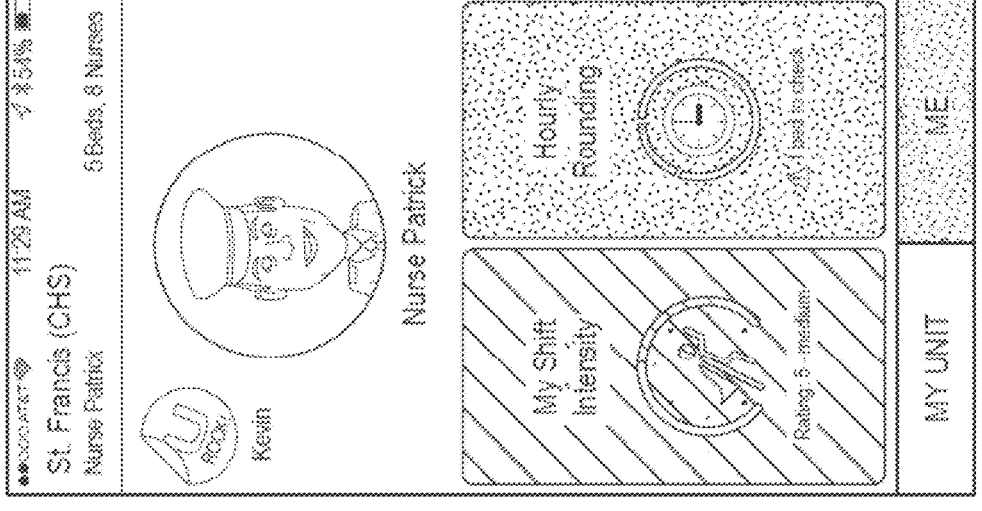
FIG. 15 is a perspective view of an illustrative embodiment of a healthcare provider main screen interface for the positioning system.

Finally, referring now to FIG. 15, there is shown an alternative illustrative embodiment of a healthcare provider main screen. In particular, the depicted embodiment is a main screen for a nurse. The main screen displays information such as the hospital name, the name of the healthcare provider (nurse), and the total number of beds and providers (nurses). The main screen also provides two analyses modules: "My Shift Intensity" and "Hourly Rounding." These analyses would be similar to the unit intensity and hourly rounding analyses provided with the healthcare management interfaces in FIGS. 12C and 13A-13C.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart aid/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

What is claimed is:

1. A system for use at a location to monitor at least one subject at the location, each subject of the at least one subject having a radio transmitter that transmits a beacon signal, the system comprising:

a base unit including a processor that is in communication with a camera and with a receiver, the receiver comprising received signal measurement electronics and at least one memory to store a threshold value; and the base unit further comprising storage with processor-executable instructions that the processor can execute to:

perform signal measurement on the beacon signal received by the receiver to indicate conditions including that the subject approached the location and that the subject moved away from the location, the signal measurement including at least a comparison of received signal to the threshold value;

collect camera information using the camera at least when the subject is indicated to have approached the location;

process the camera information to assist in tracking the subject at the location including analyzing feature data of the subject using at least some of the camera information; and process the beacon signal and the camera information to classify location transitions of the subject, wherein processing the beacon signal is constrained by the processed camera information.

2. The system of claim 1, wherein the processor-executable instructions further include instructions the processor can execute to decode an identification code in the beacon signal that is associated with the subject.

3. The system of claim 1, wherein the processor-executable instructions further include instructions the processor can execute to compare beacon signal information with at least some of the camera information to verify the identity of the subject.

4. The system of claim 1, wherein the processor-executable instructions further include instructions the processor can execute to identify position and movement of the subject at or about the location using at least the camera information.

5. The system of claim 4, wherein the processor-executable instructions further include instructions the processor can execute to create and monitor a skeletal profile of the subject.

6. The system of claim 1, wherein the base unit includes Bluetooth Low Energy (BLE) electronics.

7. The system of claim 1, wherein the received signal measurement electronics are configured to generate a received signal strength indicator (RSSI).

8. The system of claim 1, wherein the base unit further comprises a display configured to be in communication with the processor.

9. The system of claim 1, wherein the base unit further comprises a sound level detector configured to communicate with the processor.

10. The system of claim 1, wherein the base unit further comprises an ambient light sensor configured to communicate with the processor.

11. The system of claim 1, wherein the base unit further comprises a temperature sensor configured to communicate with the processor.

12. The system of claim 1, wherein the base unit further comprises a call bell detector configured to communicate with the processor.

13. The system of claim 1, wherein the base unit further comprises a pull cord detector configured to communicate with the processor.

14. A method for use at a location to monitor at least one subject at the location, each subject of the at least one subject having a radio transmitter that transmits a beacon signal, the method comprising:

using a processor and a receiver of a base unit at the location to perform signal measurement on the beacon signal received by the receiver to indicate conditions including that the subject approached the location and that the subject moved away from the location using at least a comparison of the signal measurement to a threshold value;

collect camera information using a camera of the base unit at least when the subject is indicated to have approached the location;

process the camera information to assist in tracking the subject at the location including analyzing feature data of the subject using at least some of the camera information; and process the beacon signal and the camera information to classify location transitions of the subject, wherein processing the beacon signal is constrained by the processed camera information.

15. The method of claim 14, further comprising classifying, using the processor, an activity of the subject using an output of the receiver and the camera information.

16. The method of claim 15, further comprising displaying results of the classifying on a display in communication with the base unit.

17. The method of claim 14, further comprising automatically generating a periodic skeletal profile of the subject using the camera information.

18. The method of claim 17, further comprising:

monitoring the periodic skeletal profile of the subject over time to assess a risk of developing a pressure ulcer by the subject.

19. The method of claim 17, further comprising:

monitoring the periodic skeletal profile of the subject to detect a risk of a fall of the subject.

20. The method of claim 14, further comprising calculating a position of the subject in the location using the camera information, a predetermined set of parameters associated with the subject, and a predetermined set of parameters associated with the location.

21. A non-transitory computer-readable storage medium comprising instructions for use by a base unit at a location to identify at least one subject at the location, the at least one subject having a radio transmitter that transmits a beacon signal, and the base unit having a processor in communication with a camera and a receiver, the instructions when executed by the processor include code that causes the processor to:

perform signal measurements on the beacon signal received by the receiver;

compare the signal measurements to a stored threshold value to indicate conditions including that the subject approached the location and that the subject moved away from the location;

collect camera information using the camera at least when the subject is indicated to have approached the location;

process the camera information to assist in tracking the subject at the location including analyzing feature data of the subject using at least some of the camera information; and process the beacon signal and the camera information to classify location transitions of the subject, wherein processing the beacon signal is constrained by the processed camera information.

22. The non-transitory computer-readable storage medium of claim 21, further comprising instructions that when executed by the processor cause the processor to:

generate a periodic skeletal profile of the subject using an output of the receiver and the camera information.

23. The non-transitory computer-readable storage medium of claim 22, further comprising instructions that when executed by the processor cause the processor to:

monitor the periodic skeletal profile of the subject to assess a risk of developing a pressure ulcer by the subject.

24. The non-transitory computer-readable storage medium of claim 22, further comprising instructions that when executed by the processor cause the processor to:

monitor the periodic skeletal profile of the subject to assess a risk of a fall of the subject.

25. The non-transitory computer-readable storage medium of claim 21, further comprising instructions that when executed by the processor cause the processor to:

provide an automatic notification based on the indication using a display in communication with the processor.

26. The non-transitory computer-readable storage medium of claim 21, further comprising instructions that when executed by the processor cause the processor to:

use a machine learning algorithm to process the camera information to assist in tracking the subject at the location including analyzing feature data of the subject using at least some of the camera information.

* * * * *